(12) United States Patent
Strelkova et al.

(10) Patent No.: US 12,714,756 B2
(45) Date of Patent: Aug. 25, 2026

(54) ISOLATED MODIFIED AAV9 CAPSID PROTEIN VP1

(71) Applicant: JOINT STOCK COMPANY "BIOCAD", Saint Petersburg (RU)

(72) Inventors: Anna Nikolaevna Strelkova, Yaransk (RU); Tatiana Evgenievna Shugaeva, Moscow (RU); Pavel Mikhailovich Gershovich, Saint Petersburg (RU); Pavel Andreevich Iakovlev, Saint Petersburg (RU); Dmitry Valentinovich Morozov, Saint-Petersburg (RU)

( * ) Notice: Subject to any disclaimer, the term of this patent is extended or adjusted under 35 U.S.C. 154(b) by 354 days.

(21) Appl. No.: 18/684,886

(22) PCT Filed: Aug. 21, 2022

(86) PCT No.: PCT/RU2022/050258
§ 371 (c)(1),
(2) Date: Feb. 20, 2024

(87) PCT Pub. No.: WO2023/022634
PCT Pub. Date: Feb. 23, 2023

(65) Prior Publication Data
US 2024/0350663 A1 Oct. 24, 2024

(30) Foreign Application Priority Data
Aug. 20, 2021 (RU) ................................ 2021124726

(51) Int. Cl.
*A61K 48/00* (2006.01)
*C07K 14/005* (2006.01)
*C12N 15/86* (2006.01)

(52) U.S. Cl.
CPC ........ *A61K 48/0041* (2013.01); *C07K 14/005* (2013.01); *C12N 15/86* (2013.01);
(Continued)

(58) Field of Classification Search
CPC .. A61K 48/0041; A61K 48/00; C07K 14/005; C07K 14/075; C12N 15/86;
(Continued)

(56) References Cited

U.S. PATENT DOCUMENTS

2007/0238684 A1 10/2007 Halek et al.
2015/0023924 A1 1/2015 High et al.
2016/0201088 A1 7/2016 Gao et al.

FOREIGN PATENT DOCUMENTS

JP 6042825 B2 12/2016
RU 2019126509 A1 5/2022
(Continued)

OTHER PUBLICATIONS

International application No. PCT/RU2022/050258 International Preliminary Report on Patentability Chapter I dated Feb. 13, 2024.
(Continued)

*Primary Examiner* — Christopher M Babic
*Assistant Examiner* — Thomas R. Amick
(74) *Attorney, Agent, or Firm* — Anglehart et al.

(57) ABSTRACT

The present application relates to the fields of gene therapy and molecular biology. More specifically, the present invention relates to an isolated modified capsid protein VP1 from adeno-associated virus serotype 9 (AAV9) comprising one or more amino acid substitutions compared to the wild-type AAV9 capsid protein VP1, which substitutions increase the efficiency of production (assembly) of the vector based on recombinant adeno-associated virus serotype 9 (rAAV9), to a capsid and a vector based on the above VP1, as well as to uses thereof.

21 Claims, 7 Drawing Sheets

Specification includes a Sequence Listing.

(52) U.S. Cl.
CPC .............. *C12N 2750/14122* (2013.01); *C12N 2750/14143* (2013.01); *C12N 2750/14151* (2013.01)

(58) Field of Classification Search
CPC ........... C12N 2750/14122; C12N 2750/14143; C12N 2750/14151; C12N 2750/14152; C12N 7/00; C12N 15/09; C12N 15/861
See application file for complete search history.

(56) References Cited

FOREIGN PATENT DOCUMENTS

| | | | | |
|---|---|---|---|---|
| WO | WO-2005033321 | A2 * | 4/2005 | .............. A61P 43/00 |
| WO | 2012/145601 | A2 | 10/2012 | |
| WO | 2013/158879 | A1 | 10/2013 | |
| WO | 2016/115382 | A1 | 7/2016 | |
| WO | 2017/058892 | A2 | 4/2017 | |
| WO | 2017/070516 | A1 | 4/2017 | |
| WO | 2018/152333 | A1 | 8/2018 | |
| WO | 2020/210713 | A1 | 10/2020 | |

OTHER PUBLICATIONS

International application No. PCT/RU2022/050258 International Search Report dated Jan. 19, 2023.
International application No. PCT/RU2022/050258 Written Opinion of the International Searching Authority dated Jan. 19, 2023.
NASO Michael F. et al. Adeno-Associated Virus (AAV) as a Vector for Gene Therapy. BioDrugs, 2017, v. 31(4): 317-doi: 10.1007/s40259-017-0234-5.
Xie Q. et al. The atomic structure of adeno-associated virus (AAV-2), a vector for human gene therapy. Proc Natl Acad Sci USA, 2002; 99:10405-10410.
High KA et al., "rAAV human trial experience" Methods Mol Biol. 2011; 807:429-57.
Govindasamy L. et al. Structural insights into adeno-associated virus serotype 5. J Virol. Oct. 2013; 87(20):11187-99.
Mori, S. et al., 2004, Two novel adeno-associated viruses from cynomolgus monkey: pseudotyping characterization of capsid protein, Virology, T. 330 (2): 375-83.
Sonntag F, et al. The assembly-activating protein promotes capsid assembly of different adeno-associated virus serotypes. J Virol. 2011;85(23):12686-12697. doi: 10.1128/JVI.05359-11.
Ogden PJ, et al. Comprehensive AAV capsid fitness landscape reveals a viral gene and enables machine-guided design. Science. 2019;366(6469):1139-1143. doi:10.1126/science.aaw2900.

* cited by examiner

Fig. 3
pAAV-Rep
AmpR
AAV REP GENES
pUC ORIGIN
SwaI
NotI

ISOLATED MODIFIED AAV9 CAPSID PROTEIN VP1

FIELD OF THE INVENTION

The present application relates to the fields of gene therapy and molecular biology. More specifically, the present invention relates to an isolated modified capsid protein VP1 from adeno-associated virus serotype 9 (AAV9) comprising one or more amino acid substitutions compared to the wild-type AAV9 capsid protein VP1, which substitutions increase the efficiency of production (assembly) of the vector based on recombinant adeno-associated virus serotype 9 (rAAV9), to a capsid and a vector based on the above VP1, as well as to uses thereof.

BACKGROUND OF THE INVENTION

Adeno-associated virus (AAV) is a small (25 nm), independent replication-defective, nonenveloped virus. Many different AAV serotypes have been described in human and primates. The adeno-associated virus genome is composed of (+ or −) single-stranded DNA (ssDNA) being about 4,700 nucleotides long. At the ends of a genomic DNA molecule there are accommodated terminal inverted repeats (ITRs). The genome comprises two open reading frames (ORFs): Rep and Cap comprising several alternative reading frames encoding various protein products. The rep products are essential for AAV replication, whereas three capsid proteins (VP1, VP2, and VP3), along with other alternative products, are encoded by the Cap gene. VP1, VP2, and VP3 proteins are present at 1:1:10 ratio to form an icosahedral capsid (Xie Q. et al. The atomic structure of adeno-associated virus (AAV-2), a vector for human gene therapy. Proc Natl Acad Sci USA, 2002; 99:10405-10410). During recombinant AAV (rAAV) vector production, an expression cassette flanked by ITR is packaged into an AAV capsid. The genes required for AAV replication are not included in the cassette. Recombinant AAV is considered to be one of the safest and most widely used viral vectors for in vivo gene transfer. Vectors can infect cells of multiple tissue types to provide strong and sustained transgene expression. They are also non-pathogenic, and have a low immunogenicity profile (High K A et al., "rAAV human trial experience" Methods Mol Biol. 2011; 807:429-57).

One of the urgent purposes of research in the area of development of effective gene therapy is optimization of vectors to improve certain properties of the given vectors.

The various AAV serotypes are characterized by affinity for distinct host cell surface receptors, toward which they have tropism. Thus, the primary known receptor for AAV2 is heparan sulfate proteoglycan, the coreceptors are integrin heterodimer aVβ5, fibroblast growth factor receptor type 1, and hepatocyte growth factor receptor, c-Met. AAV12 binds to heparan sulfate proteoglycans and sialic acid. AAV4 and AAV5 bind to N- and O-linked sialic acids, respectively. AAV5 activates the platelet-derived growth factor receptor. Further, a relationship has been established between the amino acid sequence of AAV capsid proteins and the process of assembly thereof, encapsidation of the genome, affinity for different types of receptors represented on the surface of host cells (Govindasamy L. et. al. Structural insights into adeno-associated virus serotype 5. J Virol. 2013 October; 87 (20): 11187-99).

The international application WO2012145601 describes adeno-associated virus (AAV) virions with variant capsid protein, where the AAV virions exhibit greater infectivity of retinal cells, when administered via intravitreal injection, compared to wild-type AAV.

The international application WO2013158879 describes an adeno-associated virus (AAV) vector for delivering to a subject a heterologous nucleic acid sequence comprising the capsid protein VP1 comprising one or more lysine substitutions, wherein one lysine substitution is K137R, wherein said lysine substitution is effective for inhibiting ubiquitination of said capsid protein, thereby increasing transduction efficiency of said AVV vector in target cells.

To date, there is a need for highly efficient production (assembly) of encapsidated viral vectors based on recombinant adeno-associated virus serotype 9 (rAAV9), i.e. for effective production of viral vectors based on recombinant adeno-associated virus serotype 9 (rAAV9) which comprise a transgene (encapsidated heterologous nucleic acid).

DESCRIPTION OF THE INVENTION

The authors of the invention have surprisingly found that the presence of one or more amino acid substitutions in the wild-type AAV9 capsid protein VP1, which are selected from the group:

F422W,

F422W and Y446F,

I601M, causes highly efficient production (assembly) of encapsidated viral vectors based on recombinant adeno-associated virus 9 (rAAV9) as compared to the assembly of encapsidated viral vectors based on wild-type rAAV9 (free of the above mutations), i.e. the assembly of encapsidated viral vectors based on rAAV9 comprising the above modifications in the AAV9 capsid results in the production of viral vectors based on rAAV9 which contain a transgene (encapsidated heterologous nucleic acid) significantly more often as compared to the assembly of encapsidated viral vectors based on wild-type rAAV9 (free of the above mutations).

BRIEF DESCRIPTION OF THE INVENTION

In one aspect, the present invention relates to an isolated modified capsid protein VP1 from adeno-associated virus serotype 9 (AAV9) for highly efficient production (assembly) of encapsidated viral vectors based on recombinant adeno-associated virus 9 (rAAV9), which comprises an amino acid sequence of the wild-type AAV9 capsid protein VP1 encoded by the Cap gene with one or more substitutions that are selected from the group:

F422W,

F422W and Y446F,

I601M, wherein the wild-type AAV9 capsid protein VP1 amino acid sequence has the amino acid sequence represented by SEQ ID NO: 1.

In some embodiments of the invention, the isolated modified AAV9 capsid protein VP1 comprises a substitution at position F422W.

In some embodiments, the isolated modified AAV9 capsid protein VP1 has the amino acid sequence represented by SEQ ID NO: 2.

In some embodiments of the invention, the isolated modified AAV9 capsid protein VP1 comprises substitutions F422W and Y446F.

In some embodiments of the invention, the isolated modified AAV9 capsid protein VP1 has the amino acid sequence represented by SEQ ID NO: 3.

In some embodiments of the invention, the isolated modified AAV9 capsid protein VP1 comprises the substitution I601M.

In some embodiments of the invention, the isolated modified AAV9 capsid protein VP1 has the amino acid sequence represented by SEQ ID NO: 4.

In one aspect, the present invention relates to an isolated nucleic acid that encodes any of the above modified capsid proteins VP1 from adeno-associated virus serotype 9 (AAV9) that are used for highly efficient production (assembly) of encapsidated viral vectors based on recombinant adeno-associated virus 9 (rAAV9).

In some embodiments of the invention, the isolated nucleic acid encodes a modified capsid protein VP1 from adeno-associated virus serotype 9 (AAV9) with the amino acid substitution F422W and is represented by a nucleic sequence with SEQ ID NO: 6 or by any other sequence encoding the respective amino acid sequence.

In some embodiments of the invention, the isolated nucleic acid encodes a modified capsid protein VP1 from adeno-associated virus serotype 9 (AAV9) with the amino acid substitutions F422W and Y446F and is represented by a nucleic sequence with SEQ ID NO: 7 or by any other sequence encoding the respective amino acid sequence.

In some embodiments of the invention, the isolated nucleic acid encodes a modified capsid protein VP1 from adeno-associated virus serotype 9 (AAV9) with the amino acid substitution I601M and is represented by a nucleic sequence with SEQ ID NO: 8 or by any other sequence encoding the respective amino acid sequence.

In one aspect, the present invention relates to an isolated capsid for highly efficient production (assembly) of encapsidated viral vectors based on recombinant adeno-associated virus 9 (rAAV9), comprising any of the above modified capsid proteins VP1 from adeno-associated virus serotype 9 (AAV9).

In some embodiments of the invention, the isolated capsid includes any of the above modified capsid proteins VP1 from adeno-associated virus serotype 9 (AAV9), AAV9 capsid protein VP2 or a modified variant thereof, and AAV9 capsid protein VP3 or a modified variant thereof.

In some embodiments of the invention, the isolated capsid includes a wild-type AAV9 capsid protein VP2.

In some embodiments of the invention, the isolated capsid includes a wild-type AAV9 capsid protein VP2, which has the amino acid sequence represented by SEQ ID NO: 9.

In some embodiments of the invention, the isolated capsid includes a modified capsid protein VP2 from adeno-associated virus serotype 9 (AAV9).

In some embodiments of the invention, the isolated capsid includes a modified AAV9 capsid protein VP2, which comprises the substitution F285W.

In some embodiments of the invention, the isolated capsid includes a modified AAV9 capsid protein VP2, which comprises the substitution F285W, and has the amino acid sequence represented by SEQ ID NO: 10.

In some embodiments of the invention, the isolated capsid includes a modified AAV9 capsid protein VP2, which comprises the substitutions F285W and Y309F.

In some embodiments of the invention, the isolated capsid includes a modified AAV9 capsid protein VP2, which comprises the substitutions F285W and Y309F, and has the amino acid sequence represented by SEQ ID NO: 11.

In some embodiments of the invention, the isolated capsid includes a modified AAV9 capsid protein VP2, which comprises the substitution I464M.

In some embodiments of the invention, the isolated capsid includes a modified AAV9 capsid protein VP2, which comprises the substitution I464M, and has the amino acid sequence represented by SEQ ID NO: 12.

In some embodiments of the invention, the isolated capsid includes a wild-type AAV9 capsid protein VP3.

In some embodiments of the invention, the isolated capsid includes a wild-type AAV9 capsid protein VP3, which has the amino acid sequence represented by SEQ ID NO: 17.

In some embodiments of the invention, the isolated capsid includes a modified capsid protein VP3 from adeno-associated virus serotype 9 (AAV9).

In some embodiments of the invention, the isolated capsid includes a modified AAV9 capsid protein VP3, which comprises the substitution F220W.

In some embodiments of the invention, the isolated capsid includes a modified AAV9 capsid protein VP3, which comprises the substitution F220W, and has the amino acid sequence represented by SEQ ID NO: 18.

In some embodiments of the invention, the isolated capsid includes a modified AAV9 capsid protein VP3, which comprises the substitutions F220W and Y244F.

In some embodiments of the invention, the isolated capsid includes a modified AAV9 capsid protein VP3, which comprises the substitutions F220W and Y244F, and has the amino acid sequence represented by SEQ ID NO: 19.

In some embodiments of the invention, the isolated capsid includes a modified AAV9 capsid protein VP3, which comprises the substitution I399M.

In some embodiments of the invention, the isolated capsid includes a modified AAV9 capsid protein VP3, which comprises the substitution I399M, and has the amino acid sequence represented by SEQ ID NO: 20.

In one aspect, the present invention relates to an isolated nucleic acid that encodes any of the above capsids that are used for highly efficient production (assembly) of encapsidated viral vectors based on recombinant adeno-associated virus 9 (rAAV9).

In one aspect, the present invention relates to a vector based on recombinant adeno-associated virus 9 (rAAV9) for delivering to a subject a heterologous nucleic acid sequence, comprising:

1) any of the above modified capsid proteins VP1 from adeno-associated virus serotype 9 (AAV9) or any of the above capsids, and
2) a heterologous nucleic acid sequence comprising regulatory sequences that promote the expression of the product encoded by the heterologous nucleic acid sequence, in the target cells.

In some embodiments of the invention, the rAAV9 vector includes a heterologous nucleic acid sequence comprising regulatory sequences that provide product expression, wherein the product of expression of the heterologous nucleic acid sequence is a therapeutic polypeptide or reporter polypeptide.

In one aspect, the present invention relates to a pharmaceutical composition for delivering a gene product to a subject in need thereof, which comprises:

a) any of the above rAAV9 vectors; and
b) a pharmaceutically acceptable excipient.

In one aspect, the present invention relates to a method for delivering a gene product to a subject in need thereof, comprising administering to the subject any of the above rAAV9 vectors or the above pharmaceutical composition.

In one aspect, the present invention relates to the use of any of the above rAAV9 vectors or the above pharmaceutical composition for treating a disease in a subject in need thereof.

In some embodiments of the use, the disease is selected from the group: blood diseases; central nervous system diseases; metabolic diseases; muscle diseases; hereditary diseases.

In one aspect, the present invention relates to a method for producing any of the above rAAV9 vectors, comprising transfecting producer cells, respectively, with any of the above nucleic acids comprising a sequence encoding a modified capsid protein VP1 from adeno-associated virus serotype 9 (AAV9), or with the above nucleic acid encoding a capsid.

GFP is a sequence encoding green fluorescent protein,

PolyA is a polyadenylation signal,

ITR is an inverted terminal repeat of adeno-associated virus,

T2A is a sequence encoding 2A self-cleaving peptide that allows co-expression of the target protein and reporter protein, HBG intron is human beta-globin intron, CMVpromoter is human cytomegalovirus promoter, AmpR is a sequence of the beta-lactamase gene that provides *E. coli* resistance to ampicillin, pUC origin is a high-copy bacterial replication origin.

Figure 2:
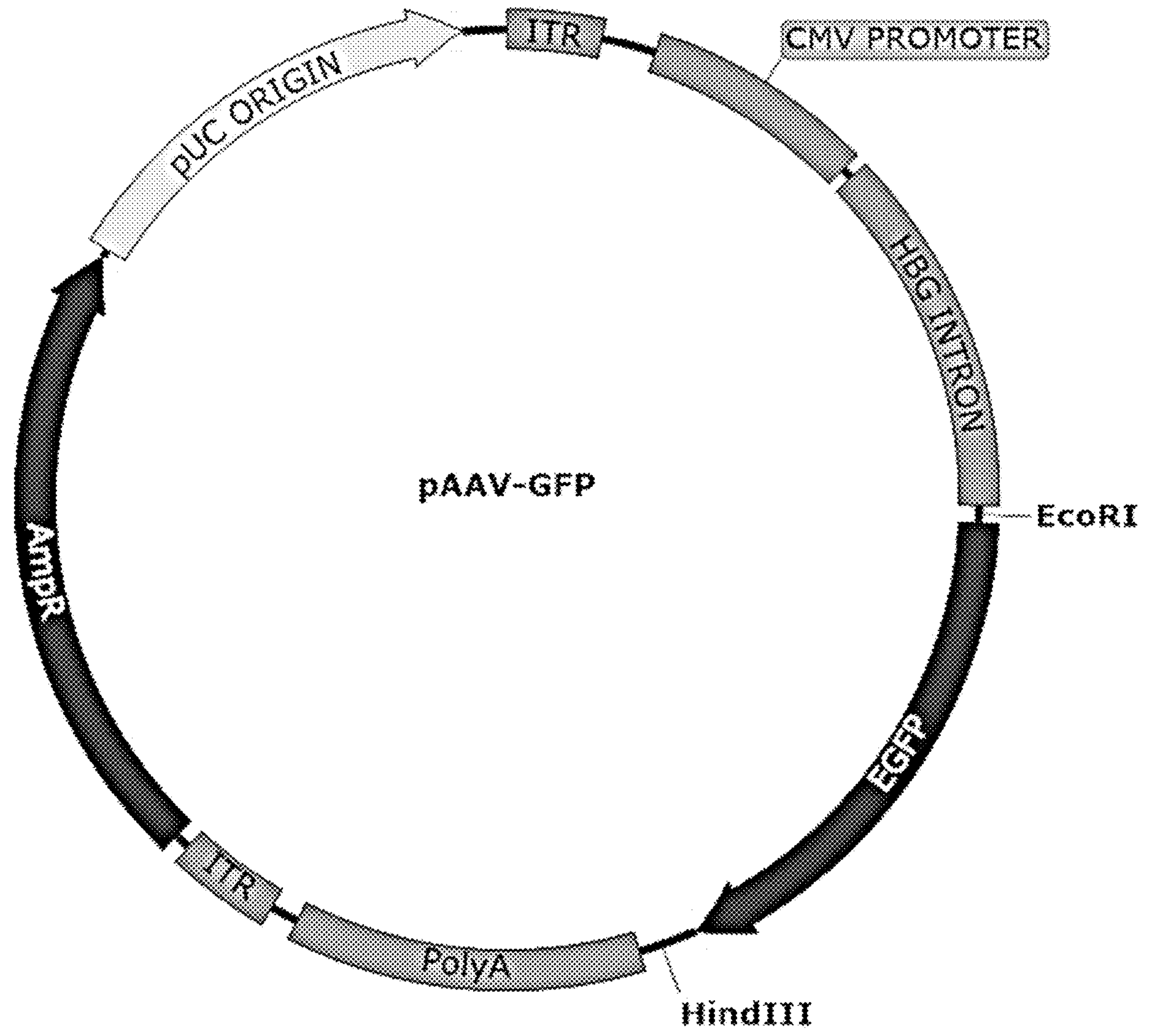

FIG. 2 is a circular diagram of the plasmid pAAV-GFP.

EGFP is a sequence encoding modified green fluorescent protein,

PolyA is a polyadenylation signal,

ITR is an inverted terminal repeat of adeno-associated virus,

HBG intron is human beta-globin intron,

CMV promoter is human cytomegalovirus promoter,

AmpR is a sequence of the beta-lactamase gene that provides E. coli resistance to ampicillin, pUC origin is a high-copy bacterial replication origin.

Figure 3:

FIG. 3 is a circular scheme of plasmid pAAV-Rep intended for producing recombinant viral products of wild-type AAV serotype 9 from the library of random variants.

AmpR is a sequence of the beta-lactamase gene that provides *E. coli* resistance to ampicillin, pUC origin is a high-copy bacterial replication origin, AAV Rep genes are a sequence encoding Rep proteins required for the virus life cycle.

Figure 4:
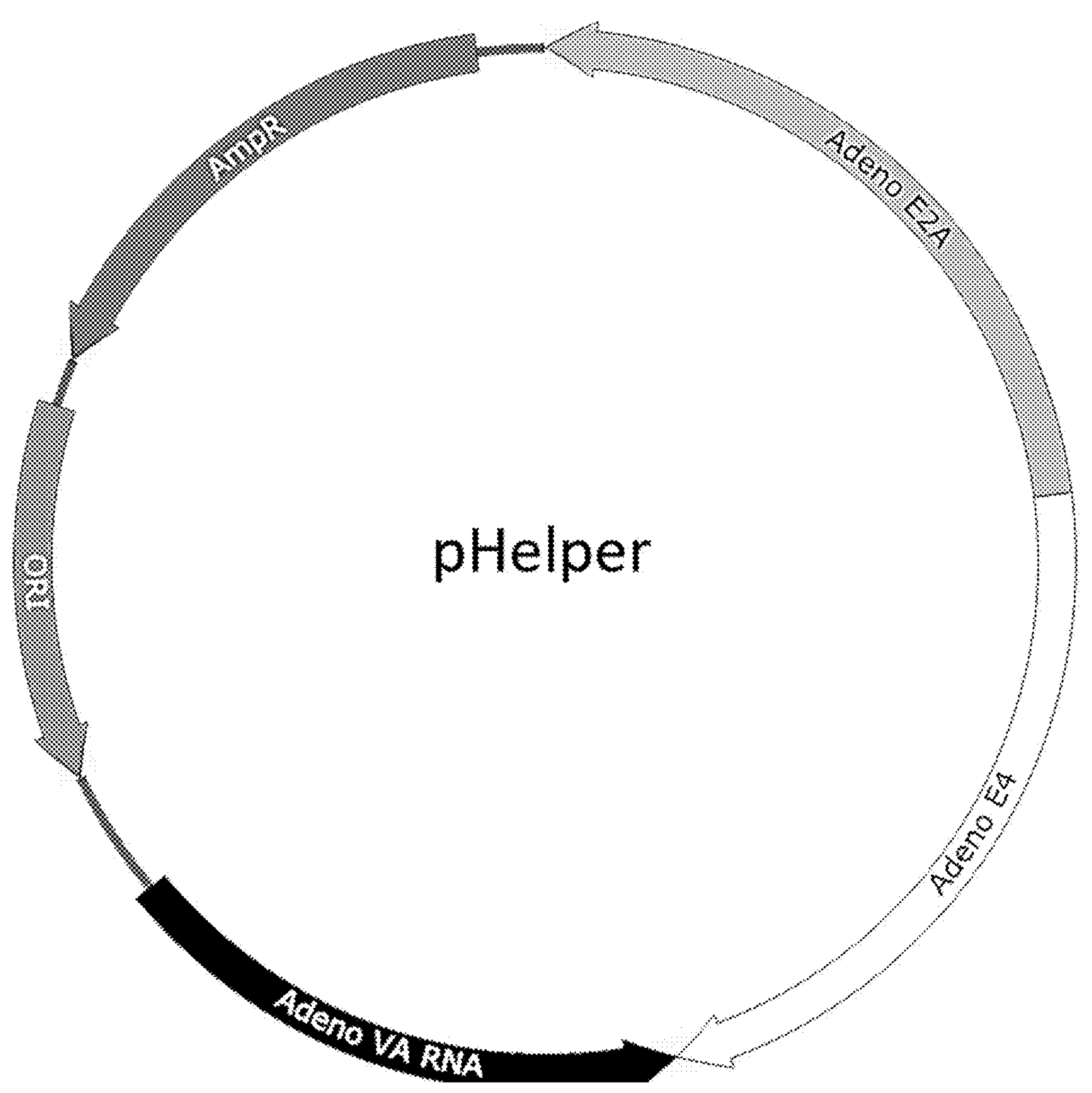

FIG. 4 is a circular scheme of plasmid pHelper intended for producing recombinant viral products of wild-type AAV serotype 9 from the library of random variants.

AmpR is a beta-lactamase gene that provides resistance to ampicillin,

Ori is a replication origin in bacteria,

Adeno E2A is a helper adenovirus gene sequence involved in viral DNA replication, Adeno E4 is a helper adenovirus gene sequence involved in viral DNA replication, Adeno VARNA is a helper adenovirus gene sequence responsible for the translation of both early and late viral genes.

Figure 5:
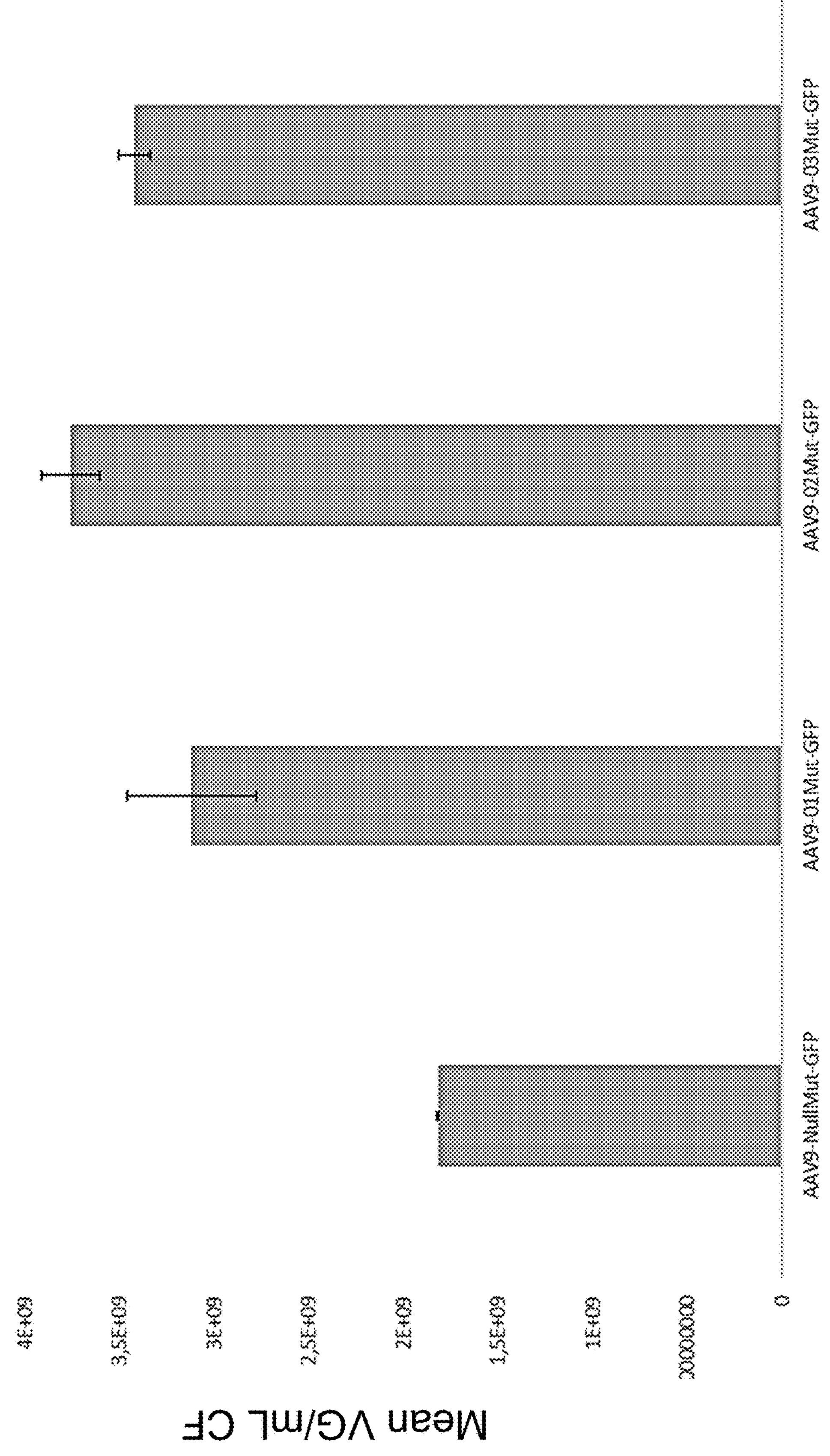

FIG. 5 is a graph showing the efficiency of of generation of vectors based on modified adeno-associated virus 9 (rAAV9) comprising a modified AAV9 capsid protein VP1.

AAV9-01Mut-GFP refers to a vector based on modified adeno-associated virus serotype 9 (rAAV9) comprising a modified AAV9 capsid protein VP1 with the mutation F422W.

AAV9-02Mut-GFP refers to a vector based on modified adeno-associated virus serotype 9 (rAAV9) comprising a modified AAV9 capsid protein VP1 with the mutation I601M.

AAV9-03Mut-GFP refers to a vector based on modified adeno-associated virus serotype 9 (rAAV9) comprising a modified AAV9 capsid protein VP1 with the mutations Y446F and F422W.

AAV9-NullMut-GFP refers to a vector based on modified adeno-associated virus serotype 9 (rAAV9) comprising a wild-type AAV9 capsid protein VP1.

Vg/ml cf refers to viral genome count per milliliter of culture fluid.

Figure 6:
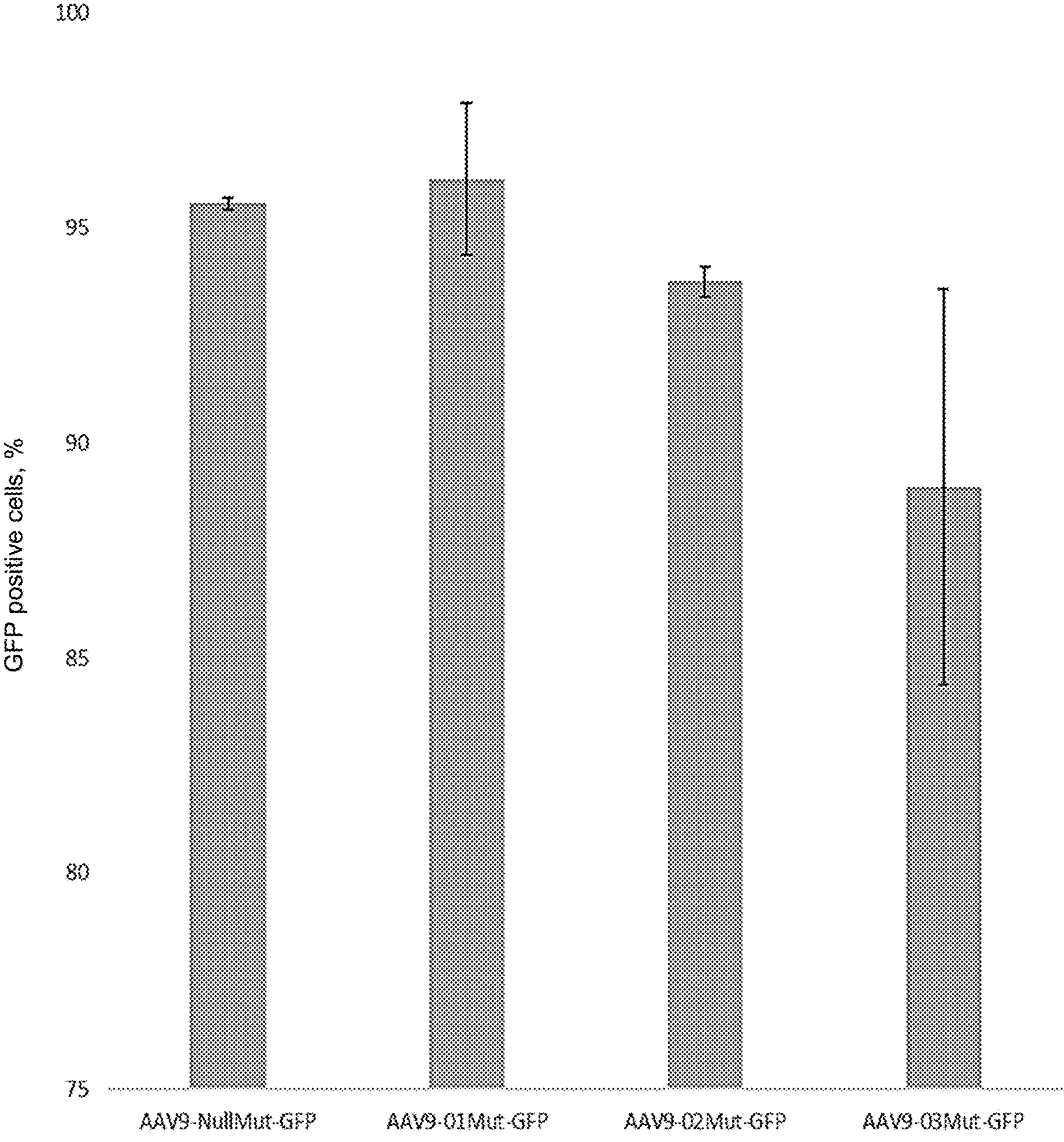

FIG. 6 is a graph showing assessment of the efficiency of cell transduction with rAAV9-based products comprising one or more point mutations in the wild-type AAV9 capsid protein VP1.

AAV9-01Mut-GFP refers to a vector based on modified adeno-associated virus serotype 9 (rAAV9) comprising a modified AAV9 capsid protein VP1 with the mutation F422W.

AAV9-02Mut-GFP refers to a vector based on modified adeno-associated virus serotype 9 (rAAV9) comprising a modified AAV9 capsid protein VP1 with the mutation I601M.

AAV9-03Mut-GFP refers to a vector based on modified adeno-associated virus serotype 9 (rAAV9) comprising a modified AAV9 capsid protein VP1 with the mutations Y446F and F422W.

AAV9-NullMut-GFP refers to a vector based on modified adeno-associated virus serotype 9 (rAAV9) comprising a wild-type AAV9 capsid protein VP1.

Figure 7:
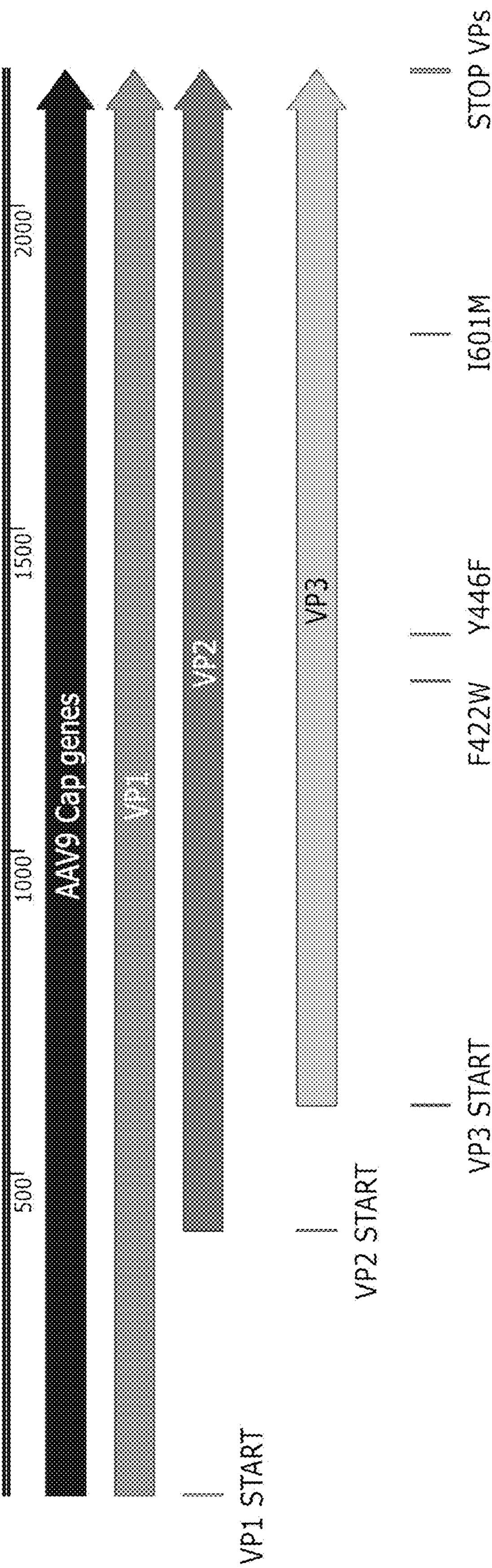

FIG. 7 is a scheme showing the position of structural proteins of the AAV9 capsid in a sequence encoding an AAV9 capsid.

1-737 aa-VP1, 138-737 aa-VP2, 203-737 aa-VP3.

DEFINITIONS AND GENERAL METHODS

Unless defined otherwise herein, all technical and scientific terms used in connection with the present invention will have the same meaning as is commonly understood by those skilled in the art.

Furthermore, unless otherwise required by context, singular terms shall include plural terms, and the plural terms shall include the singular terms. Typically, the present classification and methods of cell culture, molecular biology, immunology, microbiology, genetics, analytical chemistry, organic synthesis chemistry, medical and pharmaceutical chemistry, as well as hybridization and chemistry of protein and nucleic acids described herein are well known by those skilled and widely used in the art. Enzyme reactions and purification methods are performed according to the manufacturer's guidelines, as is common in the art, or as described herein.

"Isolated" means altered or removed from the natural state. For example, a nucleic acid or a peptide naturally present in living organisms is not "isolated" but the same nucleic acid or peptide partially or completely separated from the coexisting materials of its natural state is "isolated". An isolated nucleic acid or protein can exist substantially in purified form, or can exist in a non-native environment such as, for example, a genetically modified cell.

The terms "naturally occurring," "native," or "wild-type" are used to describe an object that can be found in nature as distinct from being artificially produced. For example, a protein or nucleotide sequence present in an organism (including a virus), which can be isolated from a source in nature and that has not been intentionally modified by a person in the laboratory, is naturally occurring.

The term "genome" refers to the complete genetic material of an organism.

As used in the present description and claims that follow, unless otherwise dictated by the context, the words "include" and "comprise," or variations thereof such as "having," "includes", "including", "comprises," or "comprising," will be understood to imply the inclusion of a stated integer or group of integers but not the exclusion of any other integer or group of integers.

Protein (Peptide)

As used in the present description, the terms "peptide", "polypeptide" and "protein" are used interchangeably, and they refer to a compound consisting of amino acid residues that are covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used in the present description, the term refers to both short chains, which also commonly are referred to in the art, for example, as peptides, oligopeptides and oligomers, and to longer chains, which generally are referred to in the art as proteins, of which there are many types. "Polypeptides" include, inter alia, for example, biologically active fragments, substantially homologous polypeptides, oligopeptides, homodimers, heterodimers, variants of polypeptides, modified polypeptides, derivatives, analogs, fusion proteins. The polypeptides include natural peptides, recombinant peptides, synthetic peptides, or a combination thereof.

Nucleic Acid Molecules

The terms "nucleic acid", "nucleic sequence", "nucleic acid sequence", "polynucleotide", "oligonucleotide", "polynucleotide sequence" and "nucleotide sequence", used interchangeably in the present description, mean a precise sequence of nucleotides, modified or not, determining a fragment or a region of a nucleic acid, containing unnatural nucleotides or not, and being either a double-strand DNA or RNA, a single-strand DNA or RNA, or transcription products of said DNAs.

As used in the present description, polynucleotides include, as non-limiting examples, all nucleic acid sequences which are obtained by any means available in the art, including, as non-limiting examples, recombinant means, i.e. the cloning of nucleic acid sequences from a recombinant library or a cell genome, using ordinary cloning technology and PCR and the like, and by synthetic means.

It should also be included here that the present invention does not relate to nucleotide sequences in their natural chromosomal environment, i.e. in a natural state. The sequences of the present invention have been isolated and/or purified, i.e., they were sampled directly or indirectly, for example by copying, their environment having been at least partially modified. Thus, isolated nucleic acids obtained by recombinant genetics, by means, for example, of host cells, or obtained by chemical synthesis should also be mentioned here.

Unless otherwise indicated, the term nucleotide sequence encompasses its complement. Thus, a nucleic acid having a particular sequence should be understood as one which encompasses the complementary strand thereof with the complementary sequence thereof.

Adeno-Associated Virus (AAV)

Viruses of the Parvoviridae family are small DNA-containing animal viruses. The Parvoviridae family may be divided into two subfamilies: the Parvovirinae, which members infect vertebrates, and the Densovirinae, which members infect insects. By 2006, there have been 11 serotypes of adeno-associated virus described (Mori, S. ET AL., 2004, "Two novel adeno-associated viruses from cynomolgus monkey: pseudotyping characterization of capsid protein", Virology, T. 330 (2): 375-83). All of the known serotypes can infect cells from multiple tissue types. Tissue specificity is determined by the capsid protein serotype; therefore, the adeno-associated virus-based vectors are constructed by assigning the desired serotype. Further information on parvoviruses and other members of the Parvoviridae is described in the literature (Kenneth I. Berns, «Parvoviridae: The Viruses and Their Replication», Chapter 69 in Fields Virology (3d Ed. 1996)).

The genomic organization of all known AAV serotypes is very similar. The genome of AAV is a linear, single-stranded DNA molecule that is less than about 5000 nucleotides (nt) in length. Inverted terminal repeats (ITR) flank unique coding nucleotide sequences of proteins (Rep) that are essential for the virus life cycle, as well as sequences of overlapping capsid proteins (Cap). The Cap gene encodes VP proteins (VP1, VP2 and VP3), which form a capsid, as well as AAP (protein activating adeno-associated virus (AAV) assembly (Sonntag F, Köther K, Schmidt K, et al. The assembly-activating protein promotes capsid assembly of different adeno-associated virus serotypes. J Virol. 2011; 85(23):12686-12697. doi:10.1128/JVI.05359-11) and MAAP (membrane-associated accessory protein (Ogden P J, Kelsic E D, Sinai S, Church G M. Comprehensive AAV capsid fitness landscape reveals a viral gene and enables machine-guided design. Science. 2019; 366(6469):1139-1143. doi:10.1126/science.aaw2900). The AAV genome flanking sequences which are 145 nucleotides long are self-complementary and are organized such that an energetically stable intramolecular duplex forming a T-shaped hairpin may be formed. Such hairpin structures function as an origin for virus DNA replication, serving as primers for the cellular DNA polymerase complex. Following wild-type AAV (wtAAV) infection in mammalian cells, the Rep genes (e.g. Rep78 and Rep52) are expressed using the P5 promoter and the P19 promoter, respectively, and the both Rep proteins have a certain function in the replication of the viral genome. A splicing event in the Rep open reading frame (Rep ORF) results in the expression of actually four Rep proteins (e.g. Rep78, Rep68, Rep52, and Rep40). However, it has been shown that the unspliced mRNA encoding Rep78 and Rep52 proteins is sufficient for AAV vector production in mammalian cells.

Recombinant Adeno-Associated Virus (rAAV)-Based Vector

The term "vector" as used herein means a nucleic acid molecule capable of transporting another nucleic acid to which it has been linked. Furthermore, the term "vector" herein refers to a viral particle capable of transporting a nucleic acid.

As used in the present description, the term “expression” is defined as the transcription and/or translation of a particular nucleotide sequence driven by its promoter.

Use

“Gene therapy” is the insertion of genes into subject’s cells and/or tissues to treat a disease, typically hereditary diseases, in which a defective mutant allele is replaced with a functional one.

“Treat”, “treating” and “treatment” refer to a method of alleviating or abrogating a biological disorder and/or at least one of its attendant symptoms. Further, references herein to “treatment” include references to curative, palliative and prophylactic treatment.

In one aspect, the subject of treatment, or patient, is a mammal, preferably a human subject. Said subject may be either male or female, of any age.

The term “disorder” means any condition that would benefit from treatment according to the present invention.

“Disease” is a state of health of a subject where the subject cannot maintain homeostasis, and where if the disease is not ameliorated then the subject’s health continues to deteriorate.

The terms “subject,” “patient,” “individual,” and the like are used interchangeably in the present description, and they refer to any animal which is amenable to the methods described in the present description. In certain non-limiting embodiments, the subject, patient or individual is a human. Said subject may be either male or female, of any age.

DETAILED DESCRIPTION OF THE INVENTION

Isolated Modified Capsid Protein VP1 from Adeno-Associated Virus Serotype 9 (AAV9)

In one aspect, the present invention relates to an isolated modified capsid protein VP1 from adeno-associated virus serotype 9 (AAV9) for highly efficient production (assembly) of encapsidated viral vectors based on recombinant adeno-associated virus 9 (rAAV9), which comprises an amino acid sequence of the wild-type AAV9 capsid protein VP1 encoded by the Cap gene with one or more substitutions that are selected from the group:

F422W,

F422W and Y446F,

I601M, wherein the wild-type AAV9 capsid protein VP1 amino acid sequence has the amino acid sequence (SEQ ID NO: 1)

MAADGYLPDWLEDNLSEGIREWWALKPGAPQPKANQQHQDNARGLVLPGY

KYLGPGNGLDKGEPVNAADAAALEHDKAYDQQLKAGDNPYLKYNHADAEF

QERLKEDTSFGGNLGRAVFQAKKRLLEPLGLVEEAAKTAPGKKRPVEQSP

QEPDSSAGIGKSGAQPAKKRLNFGQTGDTESVPDPQPIGEPPAAPSGVGS

LTMASGGGAPVADNNEGADGVGSSSGNWHCDSQWLGDRVITTSTRTWALP

TYNNHLYKQISNSTSGGSSNDNAYFGYSTPWGYFDFNRFHCHFSPRDWQR

LINNNWGFRPKRLNFKLFNIQVKEVTDNNGVKTIANNLTSTVQVFTDSDY

QLPYVLGSAHEGCLPPFPADVFMIPQYGYLTLNDGSQAVGRSSFYCLEYF

PSQMLRTGNNFQFSYEFENVPFHSSYAHSQSLDRLMNPLIDQYLYYLSKT

INGSGQNQQTLKFSVAGPSNMAVQGRNYIPGPSYRQQRVSTTVTQNNNSE

-continued

FAWPGASSWALNGRNSLMNPGPAMASHKEGEDRFFPLSGSLIFGKQGTGR

DNVDADKVMITNEEEIKTTNPVATESYGQVATNHQSAQAQAQTGWVQNQG

ILPGMVWQDRDVYLQGPIWAKIPHTDGNFHPSPLMGGFGMKHPPPQILIK

NTPVPADPPTAFNKDKLNSFITQYSTGQVSVEIEWELQKENSKRWNPEIQ

YTSNYYKSNNVEFAVNTEGVYSEPRPIGTRYLTRNL.

In some embodiments of the invention, the isolated modified AAV9 capsid protein VP1 comprises a substitution at position F422W.

In some embodiments of the invention, the isolated modified AAV9 capsid protein VP1 has the amino acid sequence (SEQ ID NO: 2)

MAADGYLPDWLEDNLSEGIREWWALKPGAPQPKANQQHQDNARGLVLPGY

KYLGPGNGLDKGEPVNAADAAALEHDKAYDQQLKAGDNPYLKYNHADAEF

QERLKEDTSFGGNLGRAVFQAKKRLLEPLGLVEEAAKTAPGKKRPVEQSP

QEPDSSAGIGKSGAQPAKKRLNFGQTGDTESVPDPQPIGEPPAAPSGVGS

LTMASGGGAPVADNNEGADGVGSSSGNWHCDSQWLGDRVITTSTRTWALP

TYNNHLYKQISNSTSGGSSNDNAYFGYSTPWGYFDFNRFHCHFSPRDWQR

LINNNWGFRPKRLNFKLFNIQVKEVTDNNGVKTIANNLTSTVQVFTDSDY

QLPYVLGSAHEGCLPPFPADVFMIPQYGYLTLNDGSQAVGRSSFYCLEYF

PSQMLRTGNNFQFSYEFENVPWHSSYAHSQSLDRLMNPLIDQYLYYLSKT

INGSGQNQQTLKFSVAGPSNMAVQGRNYIPGPSYRQQRVSTTVTQNNNSE

FAWPGASSWALNGRNSLMNPGPAMASHKEGEDRFFPLSGSLIFGKQGTGR

DNVDADKVMITNEEEIKTTNPVATESYGQVATNHQSAQAQAQTGWVQNQG

ILPGMVWQDRDVYLQGPIWAKIPHTDGNFHPSPLMGGFGMKHPPPQILIK

NTPVPADPPTAFNKDKLNSFITQYSTGQVSVEIEWELQKENSKRWNPEIQ

YTSNYYKSNNVEFAVNTEGVYSEPRPIGTRYLTRNL.

In some embodiments of the invention, the isolated modified AAV9 capsid protein VP1 comprises substitutions F422W and Y446F.

In some embodiments of the invention, the isolated modified AAV9 capsid protein VP1 has the amino acid sequence (SEQ ID NO: 3)

MAADGYLPDWLEDNLSEGIREWWALKPGAPQPKANQQHQDNARGLVLPGY

KYLGPGNGLDKGEPVNAADAAALEHDKAYDQQLKAGDNPYLKYNHADAEF

QERLKEDTSFGGNLGRAVFQAKKRLLEPLGLVEEAAKTAPGKKRPVEQSP

QEPDSSAGIGKSGAQPAKKRLNFGQTGDTESVPDPQPIGEPPAAPSGVGS

LTMASGGGAPVADNNEGADGVGSSSGNWHCDSQWLGDRVITTSTRTWALP

TYNNHLYKQISNSTSGGSSNDNAYFGYSTPWGYFDFNRFHCHFSPRDWQR

LINNNWGFRPKRLNFKLFNIQVKEVTDNNGVKTIANNLTSTVQVFTDSDY

QLPYVLGSAHEGCLPPFPADVFMIPQYGYLTLNDGSQAVGRSSFYCLEYF

PSQMLRTGNNFQFSYEFENVPWHSSYAHSQSLDRLMNPLIDQYLYFLSKT

INGSGQNQQTLKFSVAGPSNMAVQGRNYIPGPSYRQQRVSTTVTQNNNSE

FAWPGASSWALNGRNSLMNPGPAMASHKEGEDRFFPLSGSLIFGKQGTGR

-continued

DNVDADKVMITNEEEIKTTNPVATESYGQVATNHQSAQAQAQTGWVQNQG

ILPGMVWQDRDVYLQGPIWAKIPHTDGNFHPSPLMGGFGMKHPPPQILIK

NTPVPADPPTAFNKDKLNSFITQYSTGQVSVEIEWELQKENSKRWNPEIQ

YTSNYYKSNNVEFAVNTEGVYSEPRPIGTRYLTRNL.

In some embodiments of the invention, the isolated modified AAV9 capsid protein VP1 comprises the substitution I601M.

In some embodiments of the invention, the isolated modified AAV9 capsid protein VP1 has the amino acid sequence (SEQ ID NO: 4)

MAADGYLPDWLEDNLSEGIREWWALKPGAPQPKANQQHQDNARGLVLPGY

KYLGPGNGLDKGEPVNAADAAALEHDKAYDQQLKAGDNPYLKYNHADAEF

QERLKEDTSFGGNLGRAVFQAKKRLLEPLGLVEEAAKTAPGKKRPVEQSP

QEPDSSAGIGKSGAQPAKKRLNFGQTGDTESVPDPQPIGEPPAAPSGVGS

LTMASGGGAPVADNNEGADGVGSSSGNWHCDSQWLGDRVITTSTRTWALP

TYNNHLYKQISNSTSGGSSNDNAYFGYSTPWGYFDFNRFHCHFSPRDWQR

LINNNWGFRPKRLNFKLFNIQVKEVTDNNGVKTIANNLTSTVQVFTDSDY

QLPYVLGSAHEGCLPPFPADVFMIPQYGYLTLNDGSQAVGRSSFYCLEYF

PSQMLRTGNNFQFSYEFENVPFHSSYAHSQSLDRLMNPLIDQYLYYLSKT

INGSGQNQQTLKFSVAGPSNMAVQGRNYIPGPSYRQQRVSTTVTQNNNSE

FAWPGASSWALNGRNSLMNPGPAMASHKEGEDRFFPLSGSLIFGKQGTGR

DNVDADKVMITNEEEIKTTNPVATESYGQVATNHQSAQAQAQTGWVQNQG

MLPGMVWQDRDVYLQGPIWAKIPHTDGNFHPSPLMGGFGMKHPPPQILIK

NTPVPADPPTAFNKDKLNSFITQYSTGQVSVEIEWELQKENSKRWNPEIQ

YTSNYYKSNNVEFAVNTEGVYSEPRPIGTRYLTRNL.

Isolated Modified Capsid Proteins VP2 and VP3 from Adeno-Associated Virus Serotype 9 (AAV9)

The "right-hand side" of a (+)-chain of genomic DNA of adeno-associated virus comprises overlapping sequences encoding three capsid proteins: VP1, VP2 and VP3. Transcription of these genes starts from a single promoter, p40. The molecular weights of the corresponding proteins are 87, 72, and 62 kDa, respectively. All of the three proteins are translated from a single mRNA. Following transcription, pre-mRNA can be spliced in two different manners, where either longer or shorter intron is excised to form mRNAs of 2300 or 2600 nucleotide long.

Thus, the introduction of mutations into the Cap gene will affect not only the AAV9 capsid protein VP1 but also the AAV9 capsid proteins VP2 and VP3.

FIG. 7 is a schematic representation showing the position of structural proteins of the AAV9 capsid in the AAV Cap gene sequence:

1-737 aa-VP1, 138-737 aa-VP2, 203-737 aa-VP3.

With the consideration of an overlapping sequence encoding the three capsid proteins, VP1, VP2 and VP3, the amino acid substitution F422W in VP1 will correspond to:

an amino acid substitution at position F285W in VP2;

an amino acid substitution at position F220W in VP3.

With the consideration of an overlapping sequence encoding the three capsid proteins, VP1, VP2 and VP3, the amino acid substitution Y446F in VP1 will correspond to:

an amino acid substitution at position Y309F in VP2;

an amino acid substitution at position Y244F in VP3.

With the consideration of an overlapping sequence encoding the three capsid proteins, VP1, VP2 and VP3, the amino acid substitution I601M will correspond to:

an amino acid substitution at position I464M in VP2;

an amino acid substitution at position I399M in VP3.

Further, the applicant considers it appropriate to specify the environment of the mutations that have been found, by indicating a short amino acid sequence including said mutations in VP1/VP2/VP3:

For F422W in VP1 (F285W in VP2/F220W in VP3): NVPWHSS;

For Y446F in VP1 (Y309F in VP2/Y244F in VP3): YLYFLSK;

For I601M in VP1 (I464M in VP2/I399M in VP3): NQGMLPG.

In some embodiments, the amino acid sequence of a wild-type AAV9 capsid protein VP2 has the amino acid sequence represented by (SEQ ID NO: 9)

TAPGKKRPVEQSPQEPDSSAGIGKSGAQPAKKRLNFGQTGDTESVPDPQP

IGEPPAAPSGVGSLTMASGGGAPVADNNEGADGVGSSSGNWHCDSQWLGD

RVITTSTRTWALPTYNNHLYKQISNSTSGGSSNDNAYFGYSTPWGYFDFN

RFHCHFSPRDWQRLINNNWGFRPKRLNFKLFNIQVKEVTDNNGVKTIANN

LTSTVQVFTDSDYQLPYVLGSAHEGCLPPFPADVFMIPQYGYLTLNDGSQ

AVGRSSFYCLEYFPSQMLRTGNNFQFSYEFENVPFHSSYAHSQSLDRLMN

PLIDQYLYYLSKTINGSGQNQQTLKFSVAGPSNMAVQGRNYIPGPSYRQQ

RVSTTVTQNNNSEFAWPGASSWALNGRNSLMNPGPAMASHKEGEDRFFPL

SGSLIFGKQGTGRDNVDADKVMITNEEEIKTTNPVATESYGQVATNHQSA

QAQAQTGWVQNQGILPGMVWQDRDVYLQGPIWAKIPHTDGNFHPSPLMGG

FGMKHPPPQILIKNTPVPADPPTAFNKDKLNSFITQYSTGQVSVEIEWEL

QKENSKRWNPEIQYTSNYYKSNNVEFAVNTEGVYSEPRPIGTRYLTRNL.

In some embodiments of the invention, the modified AAV9 capsid protein VP2 comprises the substitution F285W.

In some embodiments of the invention, the modified AAV9 capsid protein VP2 comprises substitution F285W and has the amino acid sequence represented by (SEQ ID NO: 10)

TAPGKKRPVEQSPQEPDSSAGIGKSGAQPAKKRLNFGQTGDTESVPDPQP

IGEPPAAPSGVGSLTMASGGGAPVADNNEGADGVGSSSGNWHCDSQWLGD

RVITTSTRTWALPTYNNHLYKQISNSTSGGSSNDNAYFGYSTPWGYFDFN

RFHCHFSPRDWQRLINNNWGFRPKRLNFKLFNIQVKEVTDNNGVKTIANN

LTSTVQVFTDSDYQLPYVLGSAHEGCLPPFPADVFMIPQYGYLTLNDGSQ

AVGRSSFYCLEYFPSQMLRTGNNFQFSYEFENVPWHSSYAHSQSLDRLMN

PLIDQYLYYLSKTINGSGQNQQTLKFSVAGPSNMAVQGRNYIPGPSYRQQ

RVSTTVTQNNNSEFAWPGASSWALNGRNSLMNPGPAMASHKEGEDRFFPL

SGSLIFGKQGTGRDNVDADKVMITNEEEIKTTNPVATESYGQVATNHQSA

QAQAQTGWVQNQGILPGMVWQDRDVYLQGPIWAKIPHTDGNFHPSPLMGG

-continued

FGMKHPPPQILIKNTPVPADPPTAFNKDKLNSFITQYSTGQVSVEIEWEL

QKENSKRWNPEIQYTSNYYKSNNVEFAVNTEGVYSEPRPIGTRYLTRNL.

In some embodiments of the invention, the modified AAV9 capsid protein VP2 comprises the substitutions F285W and Y309F.

In some embodiments of the invention, the modified AAV9 capsid protein VP2 comprises the substitutions F285W and Y309F and has the amino acid sequence represented by (SEQ ID NO: 11)
TAPGKKRPVEQSPQEPDSSAGIGKSGAQPAKKRLNFGQTGDTESVPDPQP

IGEPPAAPSGVGSLTMASGGGAPVADNNEGADGVGSSSGNWHCDSQWLGD

RVITTSTRTWALPTYNNHLYKQISNSTSGGSSNDNAYFGYSTPWGYFDFN

RFHCHFSPRDWQRLINNNWGFRPKRLNFKLFNIQVKEVTDNNGVKTIANN

LTSTVQVFTDSDYQLPYVLGSAHEGCLPPFPADVFMIPQYGYLTLNDGSQ

AVGRSSFYCLEYFPSQMLRTGNNFQFSYEFENVPWHSSYAHSQSLDRLMN

PLIDQYLYFLSKTINGSGQNQQTLKFSVAGPSNMAVQGRNYIPGPSYRQQ

RVSTTVTQNNNSEFAWPGASSWALNGRNSLMNPGPAMASHKEGEDRFFPL

SGSLIFGKQGTGRDNVDADKVMITNEEEIKTTNPVATESYGQVATNHQSA

QAQAQTGWVQNQGILPGMVWQDRDVYLQGPIWAKIPHTDGNFHPSPLMGG

FGMKHPPPQILIKNTPVPADPPTAFNKDKLNSFITQYSTGQVSVEIEWEL

QKENSKRWNPEIQYTSNYYKSNNVEFAVNTEGVYSEPRPIGTRYLTRNL.

In some embodiments of the invention, the modified AAV9 capsid protein VP2 comprises the substitution I464M.

In some embodiments of the invention, the modified AAV9 capsid protein VP2 comprises the substitution I464M and has the amino acid sequence represented by (SEQ ID NO: 12)
TAPGKKRPVEQSPQEPDSSAGIGKSGAQPAKKRLNFGQTGDTESVPDPQP

IGEPPAAPSGVGSLTMASGGGAPVADNNEGADGVGSSSGNWHCDSQWLGD

RVITTSTRTWALPTYNNHLYKQISNSTSGGSSNDNAYFGYSTPWGYFDFN

RFHCHFSPRDWQRLINNNWGFRPKRLNFKLFNIQVKEVTDNNGVKTIANN

LTSTVQVFTDSDYQLPYVLGSAHEGCLPPFPADVFMIPQYGYLTLNDGSQ

AVGRSSFYCLEYFPSQMLRTGNNFQFSYEFENVPFHSSYAHSQSLDRLMN

PLIDQYLYYLSKTINGSGQNQQTLKFSVAGPSNMAVQGRNYIPGPSYRQQ

RVSTTVTQNNNSEFAWPGASSWALNGRNSLMNPGPAMASHKEGEDRFFPL

SGSLIFGKQGTGRDNVDADKVMITNEEEIKTTNPVATESYGQVATNHQSA

QAQAQTGWVQNQGMLPGMVWQDRDVYLQGPIWAKIPHTDGNFHPSPLMGG

FGMKHPPPQILIKNTPVPADPPTAFNKDKLNSFITQYSTGQVSVEIEWEL

QKENSKRWNPEIQYTSNYYKSNNVEFAVNTEGVYSEPRPIGTRYLTRNL.

In some embodiments of the invention, the wild-type AAV9 capsid protein VP3 has the amino acid sequence represented by (SEQ ID NO: 17)
MASGGGAPVADNNEGADGVGSSSGNWHCDSQWLGDRVITTSTRTWALPTY

NNHLYKQISNSTSGGSSNDNAYFGYSTPWGYFDFNRFHCHFSPRDWQRLI

NNNWGFRPKRLNFKLFNIQVKEVTDNNGVKTIANNLTSTVQVFTDSDYQL

PYVLGSAHEGCLPPFPADVFMIPQYGYLTLNDGSQAVGRSSFYCLEYFPS

QMLRTGNNFQFSYEFENVPFHSSYAHSQSLDRLMNPLIDQYLYYLSKTIN

GSGQNQQTLKFSVAGPSNMAVQGRNYIPGPSYRQQRVSTTVTQNNNSEFA

WPGASSWALNGRNSLMNPGPAMASHKEGEDRFFPLSGSLIFGKQGTGRDN

VDADKVMITNEEEIKTTNPVATESYGQVATNHQSAQAQAQTGWVQNQGIL

PGMVWQDRDVYLQGPIWAKIPHTDGNFHPSPLMGGFGMKHPPPQILIKNT

PVPADPPTAFNKDKLNSFITQYSTGQVSVEIEWELQKENSKRWNPEIQYT

SNYYKSNNVEFAVNTEGVYSEPRPIGTRYLTRNL.

In some embodiments of the invention, the modified AAV9 capsid protein VP3 comprises the substitution F220W.

In some embodiments of the invention, the modified AAV9 capsid protein VP3 comprises the substitution F220W and has the amino acid sequence represented by (SEQ ID NO: 18)
MASGGGAPVADNNEGADGVGSSSGNWHCDSQWLGDRVITTSTRTWALPTY

NNHLYKQISNSTSGGSSNDNAYFGYSTPWGYFDFNRFHCHFSPRDWQRLI

NNNWGFRPKRLNFKLFNIQVKEVTDNNGVKTIANNLTSTVQVFTDSDYQL

PYVLGSAHEGCLPPFPADVFMIPQYGYLTLNDGSQAVGRSSFYCLEYFPS

QMLRTGNNFQFSYEFENVPWHSSYAHSQSLDRLMNPLIDQYLYYLSKTIN

GSGQNQQTLKFSVAGPSNMAVQGRNYIPGPSYRQQRVSTTVTQNNNSEFA

WPGASSWALNGRNSLMNPGPAMASHKEGEDRFFPLSGSLIFGKQGTGRDN

VDADKVMITNEEEIKTTNPVATESYGQVATNHQSAQAQAQTGWVQNQGIL

PGMVWQDRDVYLQGPIWAKIPHTDGNFHPSPLMGGFGMKHPPPQILIKNT

PVPADPPTAFNKDKLNSFITQYSTGQVSVEIEWELQKENSKRWNPEIQYT

SNYYKSNNVEFAVNTEGVYSEPRPIGTRYLTRNL.

In some embodiments of the invention, the modified AAV9 capsid protein VP3 comprises the substitutions F220W and Y244F.

In some embodiments of the invention, the modified AAV9 capsid protein VP3 comprises the substitutions F220W and Y244F and has the amino acid sequence represented by (SEQ ID NO: 19)
MASGGGAPVADNNEGADGVGSSSGNWHCDSQWLGDRVITTSTRTWALPTY

NNHLYKQISNSTSGGSSNDNAYFGYSTPWGYFDFNRFHCHFSPRDWQRLI

NNNWGFRPKRLNFKLFNIQVKEVTDNNGVKTIANNLTSTVQVFTDSDYQL

PYVLGSAHEGCLPPFPADVFMIPQYGYLTLNDGSQAVGRSSFYCLEYFPS

-continued

QMLRTGNNFQFSYEFENVPWHSSYAHSQSLDRLMNPLIDQYLYFLSKTIN

GSGQNQQTLKFSVAGPSNMAVQGRNYIPGPSYRQQRVSTTVTQNNNSEFA

WPGASSWALNGRNSLMNPGPAMASHKEGEDRFFPLSGSLIFGKQGTGRDN

VDADKVMITNEEEIKTTNPVATESYGQVATNHQSAQAQAQTGWVQNQGIL

PGMVWQDRDVYLQGPIWAKIPHTDGNFHPSPLMGGFGMKHPPPQILIKNT

PVPADPPTAFNKDKLNSFITQYSTGQVSVEIEWELQKENSKRWNPEIQYT

SNYYKSNNVEFAVNTEGVYSEPRPIGTRYLTRNL.

In some embodiments of the invention, the modified AAV9 capsid protein VP3 comprises the substitution I399M.

In some embodiments of the invention, the modified AAV9 capsid protein VP3 comprises the substitution I399M and has the amino acid sequence represented by (SEQ ID NO: 20)

MASGGGAPVADNNEGADGVGSSSGNWHCDSQWLGDRVITTSTRTWALPTY

NNHLYKQISNSTSGGSSNDNAYFGYSTPWGYFDFNRFHCHFSPRDWQRLI

NNNWGFRPKRLNFKLFNIQVKEVTDNNGVKTIANNLTSTVQVFTDSDYQL

PYVLGSAHEGCLPPFPADVFMIPQYGYLTLNDGSQAVGRSSFYCLEYFPS

QMLRTGNNFQFSYEFENVPFHSSYAHSQSLDRLMNPLIDQYLYYLSKTIN

GSGQNQQTLKFSVAGPSNMAVQGRNYIPGPSYRQQRVSTTVTQNNNSEFA

WPGASSWALNGRNSLMNPGPAMASHKEGEDRFFPLSGSLIFGKQGTGRDN

VDADKVMITNEEEIKTTNPVATESYGQVATNHQSAQAQAQTGWVQNQGML

PGMVWQDRDVYLQGPIWAKIPHTDGNFHPSPLMGGFGMKHPPPQILIKNT

PVPADPPTAFNKDKLNSFITQYSTGQVSVEIEWELQKENSKRWNPEIQYT

SNYYKSNNVEFAVNTEGVYSEPRPIGTRYLTRNL.

Capsid

In one aspect, the present invention relates to an isolated capsid for highly efficient production (assembly) of encapsidated viral vectors based on recombinant adeno-associated virus 9 (rAAV9), comprising any of the above modified capsid proteins VP1 from adeno-associated virus serotype 9 (AAV9).

In some embodiments of the invention, the isolated capsid includes any of the above modified capsid proteins VP1 from adeno-associated virus serotype 9 (AAV9), AAV9 capsid protein VP2 or a modified variant thereof, and AAV9 capsid protein VP3 or a modified variant thereof.

In some embodiments of the invention, the isolated capsid includes a wild-type AAV9 capsid protein VP2.

In some embodiments of the invention, the isolated capsid includes a wild-type AAV9 capsid protein VP2, which has the amino acid sequence represented by SEQ ID NO: 9.

In some embodiments of the invention, the isolated capsid includes a modified capsid protein VP2 from adeno-associated virus serotype 9 (AAV9).

In some embodiments of the invention, the isolated capsid includes a modified AAV9 capsid protein VP2, which comprises the substitution F285W.

In some embodiments of the invention, the isolated capsid includes a modified AAV9 capsid protein VP2, which comprises the substitution F285W, and has the amino acid sequence represented by SEQ ID NO: 10.

In some embodiments of the invention, the isolated capsid includes a modified AAV9 capsid protein VP2, which comprises the substitutions F285W and Y309F.

In some embodiments of the invention, the isolated capsid includes a modified AAV9 capsid protein VP2, which comprises the substitutions F285W and Y309F, and has the amino acid sequence represented by SEQ ID NO: 11.

In some embodiments of the invention, the isolated capsid includes a modified AAV9 capsid protein VP2, which comprises the substitution I464M.

In some embodiments of the invention, the isolated capsid includes a modified AAV9 capsid protein VP2, which comprises the substitution I464M, and has the amino acid sequence represented by SEQ ID NO: 12.

In some embodiments of the invention, the isolated capsid includes a wild-type AAV9 capsid protein VP3.

In some embodiments of the invention, the isolated capsid includes a wild-type AAV9 capsid protein VP3, which has the amino acid sequence represented by SEQ ID NO: 17.

In some embodiments of the invention, the isolated capsid includes a modified capsid protein VP3 from adeno-associated virus serotype 9 (AAV9).

In some embodiments of the invention, the isolated capsid includes a modified AAV9 capsid protein VP3, which comprises the substitution F220W.

In some embodiments of the invention, the isolated capsid includes a modified AAV9 capsid protein VP3, which comprises the substitution F220W, and has the amino acid sequence represented by SEQ ID NO: 18.

In some embodiments of the invention, the isolated capsid includes a modified AAV9 capsid protein VP3, which comprises the substitutions F220W and Y244F.

In some embodiments of the invention, the isolated capsid includes a modified AAV9 capsid protein VP3, which comprises the substitutions F220W and Y244F, and has the amino acid sequence represented by SEQ ID NO: 19.

In some embodiments of the invention, the isolated capsid includes a modified AAV9 capsid protein VP3, which comprises the substitution I399M.

In some embodiments of the invention, the isolated capsid includes a modified AAV9 capsid protein VP3, which comprises the substitution I399M, and has the amino acid sequence represented by SEQ ID NO: 20.

Isolated Nucleic Acid

In one aspect, the present invention relates to an isolated nucleic acid that encodes any of the above modified capsid proteins VP1 from adeno-associated virus serotype 9 (AAV9) that are used for highly efficient production (assembly) of encapsidated viral vectors based on recombinant adeno-associated virus 9 (rAAV9).

In some embodiments of the invention, the isolated nucleic acid encodes a modified capsid protein VP1 from adeno-associated virus serotype 9 (AAV9) with the amino acid substitution F422W and is represented by a nucleic sequence with SEQ ID NO: 6 or by any other sequence encoding the respective amino acid sequence.

"Other sequence encoding the corresponding amino acid sequence of the modified capsid protein VP1 from adeno-associated virus serotype 9 (AAV9) with the amino acid substitution F422W" means a nucleic sequence that is alternative to the nucleic sequence with SEQ ID NO: 6, as, due to the degeneracy of genetic code, a wide range of different DNA sequences can encode the amino acid sequence disclosed herein as SEQ ID NO: 2. It is well within the skill of a person trained in the art to create these alternative DNA sequences encoding the same amino acid sequences. Such variant DNA sequences are within the scope of the present invention.

In some embodiments of the invention, the isolated nucleic acid encodes a modified capsid protein VP1 from adeno-associated virus serotype 9 (AAV9) with the amino acid substitutions F422W and Y446F and is represented by a nucleic sequence with SEQ ID NO: 7 or by any other sequence encoding the respective amino acid sequence.

"Other sequence encoding the corresponding amino acid sequence of the modified capsid protein VP1 from adeno-associated virus serotype 9 (AAV9) with the amino acid substitutions F422W and Y446F" means a nucleic sequence that is alternative to the nucleic sequence with SEQ ID NO: 7, as, due to the degeneracy of genetic code, a wide range of different DNA sequences can encode the amino acid sequence disclosed herein as SEQ ID NO: 3. It is well within the skill of a person trained in the art to create these alternative DNA sequences encoding the same amino acid sequences. Such variant DNA sequences are within the scope of the present invention.

In some embodiments of the invention, the isolated nucleic acid encodes a modified capsid protein VP1 from adeno-associated virus serotype 9 (AAV9) with the amino acid substitution I601M and is represented by a nucleic sequence with SEQ ID NO: 8 or by any other sequence encoding the respective amino acid sequence.

"Other sequence encoding the corresponding amino acid sequence of the modified capsid protein VP1 from adeno-associated virus serotype 9 (AAV9) with the amino acid substitution I601M" means a nucleic sequence that is alternative to the nucleic sequence with SEQ ID NO: 8, as, due to the degeneracy of genetic code, a wide range of different DNA sequences can encode the amino acid sequence disclosed herein as SEQ ID NO: 4. It is well within the skill of a person trained in the art to create these alternative DNA sequences encoding the same amino acid sequences. Such variant DNA sequences are within the scope of the present invention.

In one aspect, the present invention relates to an isolated capsid for highly efficient production (assembly) of encapsidated viral vectors based on recombinant adeno-associated virus 9 (rAAV9), comprising any of the above modified capsid proteins VP1 from adeno-associated virus serotype 9 (AAV9).

In one aspect, the present invention relates to an isolated nucleic acid encoding the above modified capsid protein VP2 from adeno-associated virus serotype 9 (AAV9).

In some embodiments of the invention, the isolated nucleic acid encodes a modified capsid protein VP2 from adeno-associated virus serotype 9 (AAV9) with the amino acid substitution F285W and is represented by a nucleic sequence with SEQ ID NO: 14 or by any other sequence encoding the respective amino acid sequence.

"Other sequence encoding the corresponding amino acid sequence of the modified capsid protein VP2 from adeno-associated virus serotype 9 (AAV9) with the amino acid substitution F285W" means a nucleic sequence that is alternative to the nucleic sequence with SEQ ID NO: 14, as, due to the degeneracy of genetic code, a wide range of different DNA sequences can encode the amino acid sequence disclosed herein as SEQ ID NO: 10. It is well within the skill of a person trained in the art to create these alternative DNA sequences encoding the same amino acid sequences. Such variant DNA sequences are within the scope of the present invention.

In some embodiments of the invention, the isolated nucleic acid encodes a modified capsid protein VP2 from adeno-associated virus serotype 9 (AAV9) with the amino acid substitutions F285W and Y309F and is represented by a nucleic sequence with SEQ ID NO: 15 or by any other sequence encoding the respective amino acid sequence.

"Other sequence encoding the corresponding amino acid sequence of the modified capsid protein VP2 from adeno-associated virus serotype 9 (AAV9) with the amino acid substitutions F285W and Y309F" means a nucleic sequence that is alternative to the nucleic sequence with SEQ ID NO: 15, as, due to the degeneracy of genetic code, a wide range of different DNA sequences can encode the amino acid sequence disclosed herein as SEQ ID NO: 11. It is well within the skill of a person trained in the art to create these alternative DNA sequences encoding the same amino acid sequences. Such variant DNA sequences are within the scope of the present invention.

In some embodiments of the invention, the isolated nucleic acid encodes a modified capsid protein VP2 from adeno-associated virus serotype 9 (AAV9) with the amino acid substitution I464M and is represented by a nucleic sequence with SEQ ID NO: 16 or by any other sequence encoding the respective amino acid sequence.

"Other sequence encoding the corresponding amino acid sequence of the modified capsid protein VP2 from adeno-associated virus serotype 9 (AAV9) with the amino acid substitution I464M" means a nucleic sequence that is alternative to the nucleic sequence with SEQ ID NO: 16, as, due to the degeneracy of genetic code, a wide range of different DNA sequences can encode the amino acid sequence disclosed herein as SEQ ID NO: 12. It is well within the skill of a person trained in the art to create these alternative DNA sequences encoding the same amino acid sequences. Such variant DNA sequences are within the scope of the present invention.

In one aspect, the present invention relates to an isolated nucleic acid encoding the above modified capsid protein VP3 from adeno-associated virus serotype 9 (AAV9).

In some embodiments of the invention, the isolated nucleic acid encodes a modified capsid protein VP3 from adeno-associated virus serotype 9 (AAV9) with the amino acid substitution F220W and is represented by a nucleic sequence with SEQ ID NO: 22 or by any other sequence encoding the respective amino acid sequence.

"Other sequence encoding the corresponding amino acid sequence of the modified capsid protein VP3 from adeno-associated virus serotype 9 (AAV9) with the amino acid substitution F220W" means a nucleic sequence that is alternative to the nucleic sequence with SEQ ID NO: 22, as, due to the degeneracy of genetic code, a wide range of different DNA sequences can encode the amino acid sequence disclosed herein as SEQ ID NO: 18. It is well within the skill of a person trained in the art to create these alternative DNA sequences encoding the same amino acid sequences. Such variant DNA sequences are within the scope of the present invention.

In some embodiments of the invention, the isolated nucleic acid encodes a modified capsid protein VP3 from adeno-associated virus serotype 9 (AAV9) with the amino acid substitutions F220W and Y244F and is represented by a nucleic sequence with SEQ ID NO: 23 or by any other sequence encoding the respective amino acid sequence.

"Other sequence encoding the corresponding amino acid sequence of the modified capsid protein VP3 from adeno-associated virus serotype 9 (AAV9) with the amino acid substitutions F220W and Y244F" means a nucleic sequence that is alternative to the nucleic sequence with SEQ ID NO: 23, as, due to the degeneracy of genetic code, a wide range of different DNA sequences can encode the amino acid sequence disclosed herein as SEQ ID NO: 19. It is well within the skill of a person trained in the art to create these alternative DNA sequences encoding the same amino acid sequences. Such variant DNA sequences are within the scope of the present invention.

In some embodiments of the invention, the isolated nucleic acid encodes a modified capsid protein VP3 from adeno-associated virus serotype 9 (AAV9) with the amino acid substitution I399M and is represented by a nucleic sequence with SEQ ID NO: 24 or by any other sequence encoding the respective amino acid sequence.

"Other sequence encoding the corresponding amino acid sequence of the modified capsid protein VP3 from adeno-associated virus serotype 9 (AAV9) with the amino acid substitution I399M" means a nucleic sequence that is alternative to the nucleic sequence with SEQ ID NO: 24, as, due to the degeneracy of genetic code, a wide range of different DNA sequences can encode the amino acid sequence disclosed herein as SEQ ID NO: 20. It is well within the skill of a person trained in the art to create these alternative DNA sequences encoding the same amino acid sequences. Such variant DNA sequences are within the scope of the present invention.

In one aspect, the present invention relates to an isolated nucleic acid that encodes any of the above capsids that are used for highly efficient production (assembly) of encapsidated viral vectors based on recombinant adeno-associated virus 9 (rAAV9).

In some embodiments, the isolated nucleic acid encoding the above capsid includes any of the above nucleic acid sequences.

Recombinant Adeno-Associated Virus 9 (rAAV9) Vector

In one aspect, the present invention relates to a vector based on recombinant adeno-associated virus 9 (rAAV9) for delivering to a subject a heterologous nucleic acid sequence, comprising:

1) any of the above modified capsid proteins VP1 from adeno-associated virus serotype 9 (AAV9) or any of the above capsids, and
2) a heterologous nucleic acid sequence comprising regulatory sequences that promote the expression of the product encoded by the heterologous nucleic acid sequence, in the target cells.

In one aspect, the present invention relates to a vector based on recombinant adeno-associated virus 9 (rAAV9) for delivering to a subject a heterologous nucleic acid sequence, comprising:

1) any of the above modified capsid proteins VP1 from adeno-associated virus serotype 9 (AAV9), and
2) a heterologous nucleic acid sequence comprising regulatory sequences that promote the expression of the product encoded by the heterologous nucleic acid sequence, in the target cells.

In one aspect, the present invention relates to a vector based on recombinant adeno-associated virus 9 (rAAV9) for delivering to a subject a heterologous nucleic acid sequence, comprising:

1) any of the above capsids, and
2) a heterologous nucleic acid sequence comprising regulatory sequences that promote the expression of the product encoded by the heterologous nucleic acid sequence, in the target cells.

The terms "vector based on recombinant adeno-associated virus serotype 9", "recombinant virus based on AAV9", "virus-like particle based on AAV9", "recombinant viral AAV9 strain", "recombinant AAV9 vector" or "vector based on rAAV9" as used in the present description have the same meaning.

In some embodiments of the invention, the rAAV9 includes a heterologous nucleic acid sequence comprising regulatory sequences that provide product expression, wherein the product of expression of the heterologous nucleic acid sequence is a therapeutic polypeptide or reporter polypeptide.

The rAAV vector according to the invention does not comprise nucleotide sequences of genes encoding sequences of proteins (Rep) that are essential for the virus life cycle, as well as sequences of overlapping capsid proteins (Cap).

The capsid is characterized in detail in the above section of the description.

"Regulatory sequences that provide the expression of product encoded by the heterologous nucleic acid sequence in target cells", as used in the present invention, mean polynucleotide sequences that are necessary to influence the expression and processing of coding sequences to which they are cloned. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include the promoter of ribosome binding site, and transcription termination sequences; in eukaryotes, typically, such control sequences include promoters and transcription termination sequences. The term "regulatory sequences" includes at least all components, the presence of which is essential for expression and processing, and can also include additional components, the presence of which is advantageous, for example, leader peptide sequences.

As used in the present description, the term "promoter" refers to a nucleic acid fragment that controls the transcription of one or more coding sequences and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art that directly or indirectly regulate the level of transcription with said promoter. A "constitutive" promoter is a promoter that is active in most tissues under typical physiological and developmental conditions. An "inducible" promoter is a promoter that is physiologically or developmentally regulated, e.g. under the influence of a chemical inducer. A "tissue specific" promoter is only active in specific types of tissues or cells.

Promoters that are used for high-level production of polypeptides in eukaryotic cells and, in particular, in mammalian cells, should be strong and preferably active in a wide range of cell types. Strong constitutive promoters which are capable of driving expression in many cell types are well known in the art and, therefore, it is not herein necessary to describe them in detail. In accordance with the idea of the present invention, it is preferable to use the cytomegalovirus (CMV) promoter. A promoter or promoter/enhancer derived from the immediate early (IE) region of human cytomegalovirus (hCMV) is particularly suitable as a promoter for the rAAV9 vector of the present invention. Human cytomegalovirus (hCMV) immediate early (IE) region and functional expression-inducing and/or functional expression-enhancing fragments derived therefrom, for example, have been disclosed in EP0173177 and EP0323997, and are well known in the art. Thus, several fragments of the hCMV immediate early (IE) region may be used as a promoter and/or promoter/enhancer.

The terms "enhancers" or "enhancer" as used herein may refer to a DNA sequence that is located adjacent to the DNA sequence that encodes a recombinant product. Enhancer elements are typically located in a 5' direction from a promoter element or can be located downstream of or within a coding DNA sequence (e.g. a DNA sequence transcribed or translated into a recombinant product or products). Hence, an enhancer element may be located 100 base pairs, 200 base pairs, or 300 or more base pairs upstream of a DNA sequence that encodes a recombinant product, or downstream of said sequence. Enhancer elements may increase the amount of a recombinant product being expressed from a DNA sequence above the level of expression associated with a single promoter element. Multiple enhancer elements are readily available to those of ordinary skill in the art.

In some embodiments of the invention, the heterologous nucleic acid sequence comprising regulatory sequences providing the expression of a product encoded by the heterologous nucleic acid sequence in target cells may include the following elements in the 5'-end to 3'-end direction:

a left-hand (first) ITR (inverted terminal repeats);

A CMV (cytomegalovirus) enhancer;

A CMV (cytomegalovirus) promoter;

an intron of the hBG1 gene (hemoglobin subunit gamma 1 gene);

a nucleic acid encoding the product;

an hGH1 polyadenylation signal (human growth hormone gene polyadenylation signal);

a right-hand (second) ITR.

In some embodiments, the nucleic acid encoding the product (transgene) is at least one gene encoding a protein. In some embodiments, the transgene encodes at least one small inhibitory nucleic acid. In some embodiments, the transgene encodes at least one reporter molecule. In some embodiments, the small inhibitory nucleic acid is miRNA. In some embodiments, the small inhibitory nucleic acid is sponge miRNA or TuD-RNA, which inhibits the activity of at least one miRNA in an animal. In some embodiments, miRNA is expressed in a cell of the target tissue. In some embodiments, the target tissue is the tissue of the liver, central nervous system (CNS), eyes, gastrointestinal tract, respiratory tract, breast, pancreas, urinary tract or uterine tissue.

In some embodiments, the rAAV9 vector has an expression product of the heterologous nucleic acid sequence, which is a therapeutic polypeptide or a reporter polypeptide.

In some embodiments, the rAAV9 vector comprises a heterologous nucleic acid sequence encoding a product that is a therapeutic polypeptide, wherein the therapeutic polypeptide is a coagulation factor selected from the group consisting of Factor VIII, Factor IX, or a functional variant thereof.

In some embodiments, the rAAV9 vector comprises a heterologous nucleic acid sequence encoding a product that is Factor VIII or a functional variant thereof.

In some embodiments, the rAAV9 vector comprises a heterologous nucleic acid sequence encoding a product that is Factor IX or a functional variant thereof.

In some embodiments, the rAAV9 vector comprises a heterologous nucleic acid sequence encoding a product that is the SMN1 protein (survival motor neuron protein)

In some embodiments, the rAAV9 vector comprises a heterologous nucleic acid sequence encoding a product that is an RBD-S polypeptide (recombinant receptor-binding domain of S glycoprotein) of SARS-cov2 (severe acute respiratory syndrome coronavirus 2).

Pharmaceutical Composition

In one aspect, the present invention relates to a pharmaceutical composition for delivering a gene product to a subject in need thereof, which comprises:

a) any of the above rAAV9 vectors; and b) a pharmaceutically acceptable excipient.

In some embodiments, the pharmaceutical composition is used for delivering a gene product to a human in need thereof.

In particular embodiments, the present invention relates to a pharmaceutical composition comprising the rAAV9 viral particle of the invention in a pharmaceutically acceptable carrier or other medicinal agents, pharmaceutical agents, carriers, adjuvants, diluents, etc. For injection, the carrier will typically be a liquid carrier. For other methods of administration, the carrier may be either solid or liquid, such as sterile pyrogen-free water or sterile pyrogen-free phosphate-buffered saline solution. For inhalation administration, the carrier is respirable, and preferably is in a solid or liquid particulate form. As an injection medium, it is preferred to use water that contains the additives that are common for injection solutions, such as stabilizing agents, salts or saline, and/or buffers.

In other embodiments, the present invention relates to a pharmaceutical composition comprising a cell, in which the rAAV9 vector is integrated into the genome, in a pharmaceutically acceptable carrier or other medicinal agents, pharmaceutical agents, carriers, adjuvants, diluents, etc.

"Pharmaceutical composition" means a composition comprising the above rAAV9 vector of the invention and at least one of components selected from the group consisting of pharmaceutically acceptable and pharmacologically compatible excipients, such as fillers, solvents, diluents, carriers, auxiliary, distributing agents, delivery agents, preservatives, stabilizers, emulsifiers, suspending agents, thickeners, prolonged delivery controllers, the choice and proportions of which depend on the type and route of administration and dosage. The pharmaceutical compositions of the present invention and methods of preparation thereof will be undoubtedly apparent to those skilled in the art. The pharmaceutical compositions should preferably be manufactured in compliance with the GMP (Good Manufacturing Practice) requirements. The composition may comprise a buffer composition, tonicity agents, stabilizers and solubilizers.

"Pharmaceutically acceptable" means a material that does not have biological or other negative side effects, for example, the material can be administered to a subject without causing any undesirable biological effects. Thus, such pharmaceutical compositions may be used, for example, in transfection of a cell ex vivo or in administration in vivo of a viral particle or a cell directly to a subject.

The term "excipient" is used herein to describe any ingredient other than the above ingredients of the invention. These are substances of inorganic or organic nature which are used in the pharmaceutical production/manufacturing in order to give drug products the necessary physicochemical properties.

"Stabilizer" refers to an excipient or a mixture of two or more excipients that provide the physical and/or chemical stability of the active agent.

The term "buffer", "buffer composition", "buffering agent" refers to a solution, which is capable of resisting changes in pH by the action of its acid-base conjugate components, which allows the rAAV9 vector product to resist changes in pH. Generally, the pharmaceutical composition preferably has a pH in the range from 4.0 to 8.0. Examples of buffers used include, but are not limited to, acetate, phosphate, citrate, histidine, succinate, etc. buffer solutions.

The pharmaceutical composition is "stable" if the active agent retains physical stability and/or chemical stability and/or biological activity thereof during the specified shelf life at storage temperature, for example, of 2-8° C. Preferably, the active agent retains both physical and chemical stability, as well as biological activity. Storage period is adjusted based on the results of stability test in accelerated or natural aging conditions.

A pharmaceutical composition according to the invention may be manufactured, packaged, or widely sold in the form of a single unit dose or a plurality of single unit doses in the form of a ready formulation. The term "single unit dose" as used herein refers to discrete quantity of a pharmaceutical composition containing a predetermined quantity of an active ingredient. The quantity of the active ingredient typically equals the dose of the active ingredient to be administered in a subject, or a convenient portion of such dose, for example, half or a third of such dose.

Method for Delivering Gene Product

In one aspect, the present invention relates to a method for delivering a gene product to a subject in need thereof, comprising administering to the subject any of the above rAAV9 vectors or the above pharmaceutical composition.

Subject refers to any living organism that is amenable to the techniques provided in the present description. In certain non-limiting embodiments, the subject is a human. Said subject may be either male or female, of any age.

Any method for administering a rAAV9 vector, which is recognized in the art, may be suitably used for the above rAAV9 vector of the present invention.

Exemplary modes of administration include topical application, intranasal, inhalation, transmucosal, transdermal, enteral (e.g. oral, rectal), parenteral (e.g. intravenous, subcutaneous, intradermal, intramuscular) administrations, as well as direct tissue or organ injections.

Injectables may be prepared in conventional forms, either as liquid solutions or suspensions, solid forms suitable for the preparation of solution or suspensions in liquid prior to injection, or as emulsions. Alternatively, one may administer the above AAV9-based recombinant virus of the present invention in a local rather than systemic manner, for example in a depot or sustained-release formulation.

The AAV9-based recombinant virus is introduced into an organism in an effective amount. The AAV9-based recombinant virus is preferably introduced into an organism in a biologically effective amount. A "biologically effective" amount of the recombinant virus is an amount that is sufficient to cause infection (or transduction) and expression of the nucleic acid sequence in the cell. If the virus is administered to a cell in vivo (e.g. the virus is administered to a subject, as described below), a "biologically-effective" amount of the viral vector is an amount that is sufficient to cause the transduction and expression of the nucleic acid sequence in the target cell.

The cell for administering the above AAV9-based recombinant virus of the invention may be a cell of any type, including but not limited to motor neurons or other tissues of the nervous system, epithelial cells (e.g. skin, respiratory and gut epithelial cells), hepatic cells, muscle cells, pancreatic cells (including islet cells), hepatic cells, spleen cells, fibroblasts, endothelial cells, and the like.

The above AAV9-based recombinant virus of the invention is not used to modify the genetic integrity of human germ line cells.

Use

In one aspect, the present invention relates to the use of any of the above rAAV9 vectors or the above pharmaceutical composition for treating a disease in a subject in need thereof.

In some embodiments of the use, the disease is selected from the group: blood diseases; central nervous system diseases; metabolic diseases; muscle diseases; hereditary diseases.

Subject refers to any animal that is amenable to the techniques provided in the present description. In certain non-limiting embodiments, the subject is a human. Said subject may be either male or female, of any age.

Administration of the rAAV9 vector of the present invention to a human subject or an animal in need thereof can be by any means known in the art for administering viral vectors.

Exemplary modes of administration include topical application, intranasal, inhalation, transmucosal, transdermal, enteral (e.g. oral, rectal), parenteral (e.g. intravenous, subcutaneous, intradermal, intramuscular) administrations, as well as direct tissue or organ injections.

Injectables may be prepared in conventional forms, either as liquid solutions or suspensions, solid forms suitable for the preparation of solution or suspensions in liquid prior to injection, or as emulsions. Alternatively, one may administer the above AAV9-based recombinant virus of the present invention in a local rather than systemic manner, for example in a depot or sustained-release formulation.

In some embodiments of the use, the disease is selected from the group comprising: blood diseases; central nervous system diseases; metabolic diseases; muscle diseases; hereditary diseases.

In some embodiments of the use, the disease is a blood disease.

In some embodiments of the use, the disease is a muscle disease.

In some embodiments of the use, the disease is a hereditary disease.

In some embodiments of the use, the expression product of the heterologous nucleic acid sequence is Factor IX or a functional variant thereof.

In some embodiments of the use, the expression product of the heterologous nucleic acid sequence is Factor VIII or a functional variant thereof.

In some embodiments of the use, the product of expression of the heterologous nucleic acid sequence is an SMN1 protein (survival motor neuron protein)

In some embodiments of the use, the product of expression of the heterologous nucleic acid sequence is an RBD-S polypeptide (recombinant receptor-binding domain of S glycoprotein) of SARS-cov2 (severe acute respiratory syndrome coronavirus 2).

In some embodiments of the use, any of the above rAAV9 vectors or the above pharmaceutical composition are used in therapeutically effective amounts.

A "therapeutically-effective amount" is understood to mean an amount that is sufficient to alleviate (e.g. mitigate, decrease, reduce) at least one of the symptoms associated with a disease state. Alternatively stated, a "therapeutically-effective" amount is an amount that is sufficient to provide some improvement in the condition of the subject.

Dosages of the above AAV9-based recombinant virus of the invention will depend on the mode of administration, the particular viral vector, and they can be determined in a routine manner. Exemplary doses for achieving therapeutic effects are viral titers of at least about $10^5$, $10^6$, $10^7$, $10^8$, $10^9$, $10^{10}$, $10^{11}$, $10^{12}$, $10^{13}$, $10^{14}$, $10^{15}$, $10^{16}$ transducing units or more, preferably about $10^9$ to $10^{15}$ transducing units, yet more preferably $10^{14}$ transducing units per kilogram.

Thus, the AAV9-based recombinant virus, reagents, and methods of the present invention can be used to direct a nucleic acid to either dividing or non-dividing cells, and to stably express the heterologous nucleic acid therein. Using this vector system, it is now possible to introduce into cells under in vivo conditions the genes that encode proteins that affect cell physiology. The vectors of the present invention can thus be useful in gene therapy for disease states.

In general, the present invention may be employed to deliver any foreign nucleic acid with a biological effect to treat or ameliorate the symptoms associated with any disorder related to gene expression. Exemplary disease states include, but are not limited to: cystic fibrosis (and other lung diseases), hemophilia A, hemophilia B, thalassemia, anemia and other blood coagulation disorders, AIDs, Alzheimer's disease, Parkinson's disease, Huntington's disease, amyotrophic lateral sclerosis, epilepsy, and other neurological disorders, diabetes mellitus, muscular dystrophies (e.g. Duchenne, Becker, spinal muscular atrophy (SMA)), Gaucher's disease, Hurler's disease, adenosine deaminase deficiency, glycogen storage diseases and other metabolic defects, diseases of solid organs (e.g. brain, liver, kidney, heart), and the like.

Gene transfer has substantial potential use in understanding and providing therapy for disease states. There are a number of hereditary diseases for which defective genes are known and have been cloned. In some cases, the function of these cloned genes is known. In general, the above disease states fall into two classes: deficiency states, typically enzyme deficiency, which are generally inherited in a recessive manner, and unbalanced states, sometimes involving at least regulatory or structural proteins, which are inherited in a dominant manner. For deficiency state diseases, gene transfer could be used to bring a normal gene into affected tissues for replacement therapy. For unbalanced disease states, gene transfer could be used to create a disease state in a model system, which could then be used in efforts to counteract the disease state. Thus, the methods of the present invention permit to treat genetic diseases. According to the invention, a disease state is treated by partially or wholly remedying the deficiency or imbalance that causes the disease or makes it more severe. The use of site-specific integration of nucleic sequences to induce mutations or to correct deficiencies is also possible.

Method for Producing rAAV9 Vector

In one aspect, the present invention relates to a method for producing any of the above rAAV9 vectors, comprising transfecting producer cells, respectively, with any of the above nucleic acids comprising a sequence encoding a modified capsid protein VP1 from adeno-associated virus serotype 9 (AAV9), or with the above nucleic acid encoding a capsid.

Capsid proteins may be expressed from a recombinant virus, an expression vector, or from a cell line into which the genes of the subject modified AAV capsids or coding sequences are stably integrated. Furthermore, the invention provides the production of AAV capsids with the described mutations in vitro from AAV capsid proteins and the construction of packaged capsids in vitro. The invention further provides the production of modified AAV capsids that have been genetically engineered to express heterologous epitopes of clinically significant antigens in order to elicit an immune response.

The method for producing the rAAV9 vector has been described in detail in the examples section.

Transgenic Animal

According to some aspects of the disclosure, provided is a method for creating a somatic transgenic animal model. In some embodiments, the method comprises administering any of the above rAAV to a non-human animal, wherein the rAAV comprises at least one transgene, and wherein the rAAV infects cells of the target tissue of a non-human animal.

In some embodiments, the use is possible of the subject capsid variants to create a somatic transgenic animal model, comprising administering any of the above rAAV to a non-human animal, wherein the rAAV comprises at least one transgene. In some embodiments, the transgene is at least one gene encoding a protein. In some embodiments, the transgene encodes at least one small inhibitory nucleic acid. In some embodiments, the transgene encodes at least one reporter molecule.

The somatic transgenic animal model may be a mammal, such as a mouse, a rat, a rabbit, a dog, a cat, a sheep, a pig, a non-human primate.

In some embodiments a putative therapeutic agent may be administered to the somatic transgenic animal model to determine the effect of the putative therapeutic agent on the disease state in the animal.

EXAMPLES

The following examples are provided for better understanding of the invention. These examples are for purposes of illustration only and are not to be construed as limiting the scope of the invention in any manner.

All publications, patents, and patent applications cited in this specification are incorporated herein by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended embodiments.

Materials and General Methods

Recombinant DNA Techniques

Standard methods were used to manipulate DNA as described in Sambrook, J. et al, Molecular cloning: A laboratory manual; Cold Spring Harbor Laboratory Press, Cold Spring Harbor, New York, 2012. The molecular biological reagents were used according to the manufacturer protocols.

Gene Synthesis

Desired gene segments were prepared from oligonucleotides made by chemical synthesis. The gene segments of 300-4,000 bp long, which were flanked by singular restriction sites, were assembled by annealing and ligation of oligonucleotides including PCR amplification and subsequently cloned via the specified restriction sites. The DNA sequences of the subcloned gene fragments were confirmed by DNA sequencing.

DNA Sequence Determination

DNA sequences were determined by Sanger sequencing.

DNA and Protein Sequence Analysis and Sequence Data Management

SnapGene software package version 5.1.4.1 was used for sequence creation, mapping, analysis, annotation and illustration.

Statistical Data Analysis

The results indicate an average value ± standard deviation (SD), analysis of variance (ANOVA) was employed to compare the test and control results, and they were determined to be statistically significant.

Example 1. Production of Libraries of rAAV9 Capsid Variants

Figure 1:
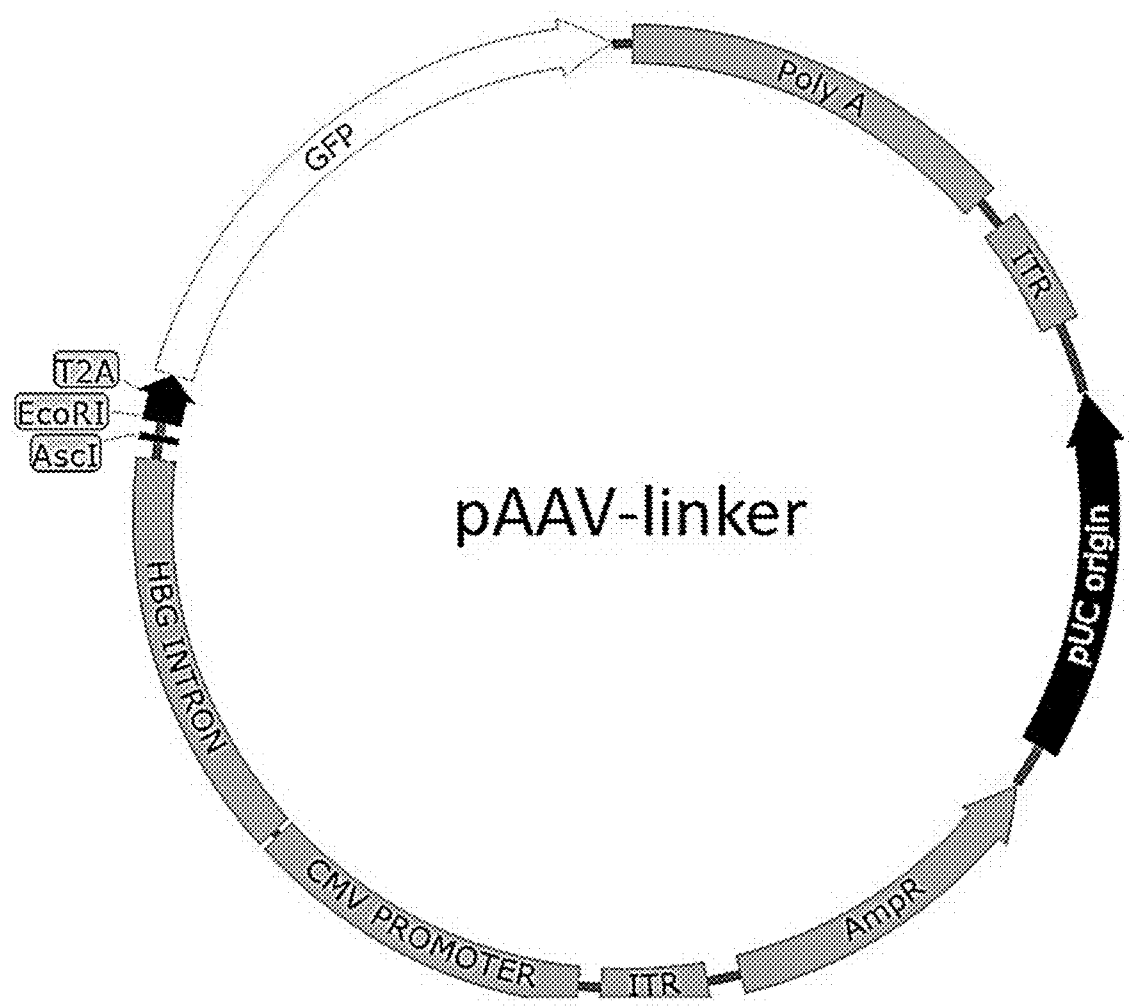
FIG. 1 is a circular scheme of plasmid pAAV-linker intended for cloning the libraries of random variants of capsid gene of AAV serotype 9.

Libraries of rAAV9 capsid variants were produced by random mutagenesis of the Cap gene sequence (Davidsson M. et al., 2016). Briefly, the wild-type sequence of the Cap gene of serotype 9 (GenBank ID AY530579.1) was assembled de novo, the synthesized wild-type AAV9 capsid nucleotide sequence was thereafter fragmented using uracil-DNA glycosylase, the resulting fragments were assembled to a full-length Cap gene using DNA polymerase not having a proofreading activity (as a result, random mutations emerged in the sequence). The full-length mutant variants were cloned into the carrier plasmid pAAV-linker (FIG. 1) at AscI/EcoRI restriction sites in a common reading frame with green fluorescent protein (GFP), thereby producing a diverse random library of rAAV9 capsids, which library was thereafter used to select capsid variants having increased assembly efficiency and/or transduction activity.

Viral particles exhibiting increased assembly efficiency were positively selected in vitro on U-87 MG cells. Further, for transduction, we used particles that were purified using ultracentrifugation in a iodixanol gradient. After 48 hours, the cells were harvested and genomic DNA was isolated for subsequent amplification of the viral genome sequences capable of efficient transduction. The resulting sequences were thereafter re-cloned and re-produced for subsequent selection iterations to enrich the library with variants having the highest assembly efficiency. After 5 rounds of selection, the capsid genes of 100 clones were sequenced to determine the most successful mutations and combinations thereof. According to the sequencing results, the predominant combinations of mutations were Y446F and F422W in AAV9 VP1 amounting to about 10% of clones, as well as clones comprising the single mutations F422W or I601M in AAV9 VP1. These capsid variants were cloned into a vector for producing viral particles and further used for visualizing and comparing the rAAV particle generation efficiency/transduction profiles relative to wild-type AAV9.

Example 2. Generation Followed by Selection of Recombinant Viral Particles from Resulting Sequence Library To produce and subsequently select recombinant viral particles from the resulting sequence library, a series of plasmids was developed as follows: a carrier plasmid, a plasmid comprising the Rep gene sequence, as well as a construct comprising adenoviral genes that are required for the replication of viral particles.

The carrier plasmid pAAV-linker (FIG. 1), intended for cloning the libraries of random variants of the capsid gene of AAV serotype 9 into one reading frame with the reporter protein, was produced by substituting the sequence of a modified green fluorescent protein in the original construct pAAV-GFP (FIG. 2), using the restrictase-ligase method of cloning at HindIII/EcoRI sites, for the sequence T2A-GFP synthesized de novo with the addition of an EcoRI restriction site from the 5' end and a HindIII restriction site from the 3' end.

The plasmid pAAV-Rep comprising the Rep gene sequence (FIG. 3) produced by de novo cloning of the synthesized AAV serotype 2 Rep gene sequence (GenBank ID AF043303.1), with the addition of a PciI restriction site at the 5' end and a PsiI restriction site at the 3' end into the plasmid pGEM-T Easy that was also treated with PciI/PsiI restrictases.

The adenoviral genes for producing the recombinant viral particles were sourced from the construct pHelper (FIG. 4), comprising AmpR—a beta-lactamase gene that provides resistance to ampicillin, Ori—a replication origin in bacteria, Adeno E2A—a helper adenovirus gene sequence involved in viral DNA replication, Adeno E4—a helper adenovirus gene sequence involved in viral DNA replication, Adeno VARNA—a helper adenovirus gene sequence responsible for the translation of both early and late viral genes.

Example 3. Efficiency of Generation of Vectors Based on Modified Adeno-Associated Virus 9 (rAAV9)

To produce rAAV particles with the modified serotype 9 capsid, HEK293 producer cells were transfected using polyethylenimine simultaneously with 3 plasmids as follows:

1) With a plasmid comprising adenovirus nucleotide sequences coding proteins and RNAs required for assembly of rAAV particles (helper plasmid);
2) With a plasmid comprising the natural nucleotide sequence of the Rep gene of adeno-associated virus, as well as the sequence of modified Cap gene, which is selected from the group: the nucleotide sequence of SEQ ID NO: 6, 7 or 8 or any other nucleotide sequence encoding the VP1 protein with the amino acid sequences of SEQ ID No: 2, 3 or 4, and the VP2 and VP3 proteins from alternative reading frames of the nucleotide sequence being used, wherein
   - the VP2 can have any of the amino acid sequences of SEQ ID No: 9, 10, 11 or 12;
   - and the VP3 can have any of the amino acid sequences of SEQ ID No: 17, 18, 19 or 20;
3) With a plasmid comprising the heterologous rAAV particle genome encoding a target gene intended for delivery into patient's cells.

This set of genes provides the assembly of rAAV viral particles and encapsidation of the target genome therein within 72 hours. 72 hours following transfection, the producing cells were subjected to lysis to release rAAV particles, the resulting vectors were treated with DNAase I for 2 hours at 37° C., and then for another 2 hours with proteinase K at 56° C. The titer of the resulting rAAV particles was determined by quantitative PCR using an oligonucleotide set consisting of a forward primer 5'-AC-CACATGAAGCAGCACGAC-3', a reverse primer 5'-TCAGCTCGATGCGGTTCAC-3', and a probe 5'-HEX-CATGCCCGAAGGCTACGTCCAG-BHQ1-3' specific for the GFP sequence.

The authors of the invention surprisingly found that the presence of a single substitution selected from the group including: F422W or I601M, or the simultaneous presence of the mutations Y446F and F422W in the wild-type AAV9 capsid protein VP1 led to a significant increase in the yield of encapsidated viral particles based on rAAV9 with the above mutations. For example, quantitative PCR showed a change in copy number of the packaged heterologous rAAV particle genome encoding the target GFP gene (FIG. 5).

In the presence of the mutation F422W (AAV9-01Mut-GFP), the number of packaged viral genomes increased by 1.71 times from 1.82E+09 vg/ml to 3.12E+09 vg/ml as compared to the control AAV9 with the wild-type capsid protein VP1 (AAV9-NullMut-GFP).

In the presence of the mutation I601M (AAV9-02Mut-GFP), the number of packaged viral genomes increased by 2.1 times from 1.82E+09 vg/ml to 3.76E+09 vg/ml as compared to the control AAV9 with the wild-type capsid protein VP1 (AAV9-NullMut-GFP).

In the simultaneous presence of the mutations Y446F and F422W (AAV9-03Mut-GFP), the number of packaged viral genomes increased by 1.88 times from 1.82E+09 vg/ml to 3.42E+09 vg/ml as compared to the control AAV9 with the wild-type capsid protein VP1 (AAV9-NullMut-GFP).

Example 4. Evaluation of Efficiency of Cell Transduction with rAAV9-based Products Comprising Point Mutations in Wild-Type AAV9 Capsid Protein VP1

U-87 MG cells were plated into wells of 24-well plates. The cells were plated into a EMEM growth medium supplemented with glutamine, 10% bovine serum. Cell seeding density was 10,000 cell/cm$^2$. During the transduction run, pre-prepared cells were transduced at MOI of 400,000 vg/cell. All samples were run in triplicates. Intact cells were used as a negative control.

Transduction efficiency was measured by intensity of the GFP reporter protein signal using a Guava EasyCyte flow cytometer and GuavaSoft software.

The authors of the invention found that the presence of the single mutation F422W or I601M as well as the simultaneous presence of the mutations Y446F and F422W in the wild-type AAV9 capsid protein VP1 did not lead to a significant decrease in the efficiency of transgene delivery by the rAAV vectors with the above mutations. For example, flow cytometry revealed a change in the number of GFP positive cells 48 hours following transduction of U-87 MG cell line with rAAV-based products with the wild-type AAV9 capsid protein VP1 or the wild-type AAV9 capsid protein VP1 comprising the single mutation F422W or I601M, as well as capsid variants simultaneously comprising the mutations Y446F and F422W in the wild-type AAV9 capsid protein VP1 (FIG. 6).

With the control rAAV9 product with the wild-type capsid protein VP1 (AAV9-NullMut-GFP), the number of cells expressing GFP was 95.58%.

In the presence of the mutation F422W (AAV9-01Mut-GFP), the number of cells expressing GFP was 96.15%.

In the presence of the mutation I601M (AAV9-02Mut-GFP), the number of cells expressing GFP was 93.75%.

In the simultaneous presence of the mutations Y446F and F422W (AAV9-03Mut-GFP)

The invention claimed is:

1. An isolated modified capsid protein VP1 from adeno-associated virus serotype 9 (AAV9) for production of encapsidated viral vectors based on recombinant adeno-associated virus serotype 9 (rAAV9), said isolated modified capsid protein VP1 comprising a wild-type AAV9 capsid protein VP1 amino acid sequence encoded by the Cap gene with one or more substitutions that are selected from the group consisting of:

F422W,

F422W and Y446F, and

I601M, wherein the wild-type AAV9 capsid protein VP1 amino acid sequence has the amino acid sequence represented by SEQ ID NO: 1.

2. The isolated modified AAV9 capsid protein VP1 according to claim 1, comprising a substitution at position F422W.

3. The isolated modified AAV9 capsid protein VP1 according to claim 2, comprising the amino acid sequence represented by SEQ ID NO: 2.

4. The isolated modified AAV9 capsid protein VP1 according to claim 1, comprising the substitutions F422W and Y446F.

5. The isolated modified AAV9 capsid protein VP1 according to claim 4, comprising the amino acid sequence represented by SEQ ID NO: 3.

6. The isolated modified AAV9 capsid protein VP1 according to claim 1, comprising the substitution I601M.

7. The isolated modified AAV9 capsid protein VP1 according to claim 6, comprising the amino acid sequence represented by SEQ ID NO: 4.

8. An isolated nucleic acid encoding the modified capsid protein VP1 from adeno-associated virus serotype 9 according to claim 1, wherein said capsid protein VP1 is adapted for production of encapsidated viral vectors based on recombinant adeno-associated virus serotype 9.

9. An isolated capsid for production of encapsidated viral vectors based on recombinant adeno-associated virus serotype 9, said isolated capsid including the modified capsid protein VP1 from adeno-associated virus serotype 9 according to claim 1.

10. The isolated capsid according to claim 9, comprising the AAV9 capsid protein VP2 or a modified variant thereof, and the AAV9 capsid protein VP3 or a modified variant thereof.

11. The isolated capsid according to claim 10, comprising a wild-type AAV9 capsid protein VP2 comprising the amino acid sequence represented by SEQ ID NO: 9.

12. The isolated capsid according to claim 10, comprising a modified AAV9 capsid protein VP2 comprising:

the substitution F285W;

the substitutions F285W and Y309F; or the substitution I464M.

13. The isolated capsid according to claim 12, comprising a modified AAV9 capsid protein VP2 comprising the substitution F285W and having comprising:

an amino acid sequence represented by SEQ ID NO: 10;

a modified AAV9 capsid protein VP2 comprising the substitution F285W and Y309F and comprising an amino acid sequence represented by SEQ ID NO: 11; or a modified AAV9 capsid protein VP2 comprising the substitution 1464M and comprising an amino acid sequence represented by SEQ ID NO: 12.

14. The isolated capsid according to claim 10, comprising a wild-type AAV9 capsid protein VP3 that comprises an amino acid sequence represented by SEQ ID NO: 17.

15. The isolated capsid according to claim 10, comprising a modified AAV9 capsid protein from adeno-associated virus serotype 9 VP3 comprising the substitution F220W or comprising the substitutions F220W and Y244F or comprising the substitution I399M.

16. The isolated capsid according to claim 15, comprising a modified AAV9 capsid protein VP3 comprising the substitution F220W and comprising:

an amino acid sequence represented by SEQ ID NO: 18;

a modified AAV9 capsid protein VP3 comprising the substitutions F220W and Y244F, and comprising an amino acid sequence represented by SEQ ID NO: 19; or a modified AAV9 capsid protein VP3 comprising the substitution 1399M and comprising an amino acid sequence represented by SEQ ID NO: 20.

17. An isolated nucleic acid encoding the capsid according to claim 9, wherein said capsid is for highly efficient production of encapsidated viral vectors based on recombinant adeno-associated virus serotype 9.

18. A vector based on recombinant adeno-associated virus serotype 9 for delivering a heterologous nucleic acid sequence to a subject, said vector comprising:

1) the modified capsid protein VP1 from adeno-associated virus serotype 9 according to claim 1 or an isolated capsid for production of encapsidated viral vectors based on recombinant adeno-associated virus serotype 9, said isolated capsid including the modified capsid protein VP1 from adeno-associated virus serotype 9, and 2) a heterologous nucleic acid sequence comprising regulatory sequences that promote the expression of the product encoded by the heterologous nucleic acid sequence, in the target cells.

19. A pharmaceutical composition for the delivery of a gene product to a subject in need thereof, comprising:

a) the rAAV9 vector according to claim 18; and b) a pharmaceutically acceptable excipient.

20. A method for delivering a gene product to a subject in need thereof, comprising administering to the subject the rAAV9 vector or the pharmaceutical composition according to claim 19.

21. A method for producing the rAAV9 vector according to claim 18, comprising transfection of producer cells, respectively, with a nucleic acid comprising a sequence encoding a modified capsid protein VP1 from adeno-associated virus serotype 9, or with a nucleic acid encoding a capsid for production of encapsidated viral vectors based on recombinant adeno-associated virus serotype 9, said isolated capsid including the modified capsid protein VP1 from adeno-associated virus serotype 9.

* * * * *

SEQUENCE LISTING

```
Sequence total quantity: 24
SEQ ID NO: 1            moltype = AA  length = 736
FEATURE                 Location/Qualifiers
source                  1..736
                        mol_type = protein
                        organism = Adeno-associated dependoparvovirus A
SEQUENCE: 1
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                  736

SEQ ID NO: 2            moltype = AA  length = 736
FEATURE                 Location/Qualifiers
source                  1..736
                        mol_type = protein
                        organism = synthetic construct
SEQUENCE: 2
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PWHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                  736
```

```
SEQ ID NO: 3            moltype = AA  length = 736
FEATURE                 Location/Qualifiers
source                  1..736
                        mol_type = protein
                        organism = synthetic construct
SEQUENCE: 3
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PWHSSYAHSQ SLDRLMNPLI DQYLYFLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 4            moltype = AA  length = 736
FEATURE                 Location/Qualifiers
source                  1..736
                        mol_type = protein
                        organism = synthetic construct
SEQUENCE: 4
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
MLPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 5            moltype = DNA  length = 2211
FEATURE                 Location/Qualifiers
source                  1..2211
                        mol_type = genomic DNA
                        organism = Adeno-associated dependoparvovirus A
SEQUENCE: 5
atggctgccg atggttatct tccagattgg ctcgaggaca accttagtga aggaattcgc  60
gagtggtggg ctttgaaacc tggagcccct caacccaagg caaatcaaca acatcaagac  120
aacgctcgag gtcttgtgct tccgggttac aaataccttg gacccggcaa cggactcgac  180
aagggggagc cggtcaacgc agcagacgcg gcggccctcg agcacgacaa ggcctacgac  240
cagcagctca aggccggaga caacccgtac ctcaagtaca accacgccga cgccgagttc  300
caggagcggc tcaaagaaga tacgtctttt gggggcaacc tcgggcgagc agtcttccag  360
gccaaaaaga ggcttcttga acctcttggt ctggttgagg aagcggctaa gacggctcct  420
ggaaagaaga ggcctgtaga gcagtctcct caggaaccgg actcctccgc gggtattggc  480
aaatcgggtg cacagcccgc taaaaagaga ctcaatttcg gtcagactgg cgacacagag  540
tcagtcccag accctcaacc aatcggagaa cctcccgcag ccccctcagg tgtgggatct  600
cttacaatgg cttcaggtgg tggcgcacca gtggcagaca ataacgaagg tgccgatgga  660
gtgggtagtt cctcgggaaa ttggcattgc gattcccaat ggctggggga cagagtcatc  720
accaccagca cccgaacctg ggccctgccc acctacaaca atcacctcta caagcaaatc  780
tccaacagca catctggagg atcttcaaat gacaacgcct acttcggcta cagcaccccc  840
tgggggtatt ttgacttcaa cagattccac tgccacttct caccacgtga ctggcagcga  900
ctcatcaaca acaactgggg attccggcct aagcgactca acttcaagct cttcaacatt  960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caaagaagga gaggaccgtt tctttccttt gtctggatct  1620
ttaatttttg gcaaacaagg aactggaaga gacaacgtgg atgcggacaa agtcatgata  1680
accaacgaag aagaaattaa aactactaac ccggtagcaa cggagtccta tggacaagtg  1740
gccacaaacc accagagtgc ccaagcacag gcgcagaccg gctgggttca aaaccaagga  1800
atacttccgg gtatggtttg gcaggacaga gatgtgtacc tgcaaggacc catttgggcc  1860
aaaattcctc acacggacgg caactttcac ccttctccgc tgatgggagg gtttggaatg  1920
```

```
aagcacccgc ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa aacagcaagc gctggaaccc ggagatccag  2100
tacacttcca actattacaa gtctaataat gttgaatttg ctgttaatac tgaaggtgta  2160
tatagtgaac cccgccccat tggcaccaga tacctgactc gtaatctgta a           2211

SEQ ID NO: 6            moltype = DNA  length = 2211
FEATURE                 Location/Qualifiers
source                  1..2211
                        mol_type = other DNA
                        organism = synthetic construct
SEQUENCE: 6
atggctgccg atggttatct tccagattgg ctcgaggaca accttagtga aggaattcgc  60
gagtggtggg ctttgaaacc tggagcccct caacccaagg caaatcaaca acatcaagac  120
aacgctcgag gtcttgtgct tccgggttac aaataccttg gacccggcaa cggactcgac  180
aagggggagc cggtcaacgc agcagacgcg gcggccctcg agcacgacaa ggcctacgac  240
cagcagctca aggccggaga caacccgtac ctcaagtaca accacgccga cgccgagttc  300
caggagcggc tcaaagaaga tacgtctttt gggggcaacc tcgggcgagc agtcttccag  360
gccaaaaaga ggcttcttga acctcttggt ctggttgagg aagcggctaa gacggctcct  420
ggaaagaaga ggcctgtaga gcagtctcct caggaaccgg actcctccgc gggtattggc  480
aaatcgggtg cacagcccgc taaaaagaga ctcaatttcg gtcagactgg cgacacagag  540
tcagtcccag accctcaacc aatcggagaa cctcccgcag ccccctcagg tgtgggatct  600
cttacaatgg cttcaggtgg tggcgcacca gtggcagaca ataacgaagg tgccgatgga  660
gtgggtagtt cctcgggaaa ttggcattgc gattcccaat ggctgggga cagagtcatc  720
accaccagca cccgaacctg ggccctgccc acctacaaca atcacctcta caagcaaatc  780
tccaacagca catctggagg atcttcaaat gacaacgcct acttcggcta cagcaccccc  840
tgggggtatt ttgacttcaa cagattccac tgccacttct caccacgtga ctggcagcga  900
ctcatcaaca acaactgggg attccggcct aagcgactca acttcaagct cttcaacatt  960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
ccttggcata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caaagaagga gaggaccgtt tctttccttt gtctggatct  1620
ttaatttttg gcaaacaagg aactggaaga gacaacgtgg atgcggacaa agtcatgata  1680
accaacgaag aagaaattaa aactactaac ccggtagcaa cggagtccta tggacaagtg  1740
gccacaaacc accagagtgc ccaagcacag gcgcagaccg gctgggttca aaaccaagga  1800
atacttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcacccgc ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa aacagcaagc gctggaaccc ggagatccag  2100
tacacttcca actattacaa gtctaataat gttgaatttg ctgttaatac tgaaggtgta  2160
tatagtgaac cccgccccat tggcaccaga tacctgactc gtaatctgta a           2211

SEQ ID NO: 7            moltype = DNA  length = 2211
FEATURE                 Location/Qualifiers
source                  1..2211
                        mol_type = other DNA
                        organism = synthetic construct
SEQUENCE: 7
atggctgccg atggttatct tccagattgg ctcgaggaca accttagtga aggaattcgc  60
gagtggtggg ctttgaaacc tggagcccct caacccaagg caaatcaaca acatcaagac  120
aacgctcgag gtcttgtgct tccgggttac aaataccttg gacccggcaa cggactcgac  180
aagggggagc cggtcaacgc agcagacgcg gcggccctcg agcacgacaa ggcctacgac  240
cagcagctca aggccggaga caacccgtac ctcaagtaca accacgccga cgccgagttc  300
caggagcggc tcaaagaaga tacgtctttt gggggcaacc tcgggcgagc agtcttccag  360
gccaaaaaga ggcttcttga acctcttggt ctggttgagg aagcggctaa gacggctcct  420
ggaaagaaga ggcctgtaga gcagtctcct caggaaccgg actcctccgc gggtattggc  480
aaatcgggtg cacagcccgc taaaaagaga ctcaatttcg gtcagactgg cgacacagag  540
tcagtcccag accctcaacc aatcggagaa cctcccgcag ccccctcagg tgtgggatct  600
cttacaatgg cttcaggtgg tggcgcacca gtggcagaca ataacgaagg tgccgatgga  660
gtgggtagtt cctcgggaaa ttggcattgc gattcccaat ggctgggga cagagtcatc  720
accaccagca cccgaacctg ggccctgccc acctacaaca atcacctcta caagcaaatc  780
tccaacagca catctggagg atcttcaaat gacaacgcct acttcggcta cagcaccccc  840
tgggggtatt ttgacttcaa cagattccac tgccacttct caccacgtga ctggcagcga  900
ctcatcaaca acaactgggg attccggcct aagcgactca acttcaagct cttcaacatt  960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
ccttggcata gcagctacgc tcacagccaa agcctggacc gactaatgaa tccactcatc  1320
gaccaatact tgtactttct ctcaaagact attaacggtt ctggacagaa tcaacaaacg  1380
```

```
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caaagaagga gaggaccgtt tctttccttt gtctggatct  1620
ttaattttg gcaaacaagg aactggaaga gacaacgtgg atgcggacaa agtcatgata  1680
accaacgaag aagaaattaa aactactaac ccggtagcaa cggagtccta tggacaagtg  1740
gccacaaacc accagagtgc ccaagcacag gcgcagaccg gctgggttca aaaccaagga  1800
atacttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcacccgc ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa aacagcaagc gctggaaccc ggagatccag  2100
tacacttcca actattacaa gtctaataat gttgaatttg ctgttaatac tgaaggtgta  2160
tatagtgaac cccgccccat tggcaccaga tacctgactc gtaatctgta a           2211

SEQ ID NO: 8             moltype = DNA  length = 2211
FEATURE                  Location/Qualifiers
source                   1..2211
                         mol_type = other DNA
                         organism = synthetic construct
SEQUENCE: 8
atggctgccg atggttatct tccagattgg ctcgaggaca accttagtga aggaattcgc  60
gagtggtggg ctttgaaacc tggagcccct caacccaagg caaatcaaca acatcaagac  120
aacgctcgag gtcttgtgct tccgggttac aaataccttg gacccggcaa cggactcgac  180
aagggggagc cggtcaacgc agcagacgcg gcggccctcg agcacgacaa ggcctacgac  240
cagcagctca aggccggaga caacccgtac ctcaagtaca accacgccga cgccgagttc  300
caggagcggc tcaaagaaga tacgtctttt gggggcaacc tcgggcgagc agtcttccag  360
gccaaaaaga ggcttcttga acctcttggt ctggttgagg aagcggctaa gacggctcct  420
ggaaagaaga ggcctgtaga gcagtctcct caggaaccgg actcctccgc gggtattggc  480
aaatcgggtg cacagcccgc taaaaagaga ctcaatttcg gtcagactgg cgacacagag  540
tcagtcccag accctcaacc aatcggagaa cctcccgcag ccccctcagg tgtgggatct  600
cttacaatgg cttcaggtgg tggcgcacca gtggcagaca ataacgaagg tgccgatgga  660
gtgggtagtt cctcgggaaa ttggcattgc gattcccaat ggctggggga cagagtcatc  720
accaccagca cccgaacctg ggccctgccc acctacaaca atcacctcta caagcaaatc  780
tccaacagca catctggagg atcttcaaat gacaacgcct acttcggcta cagcaccccc  840
tgggggtatt ttgacttcaa cagattccac tgccacttct caccacgtga ctggcagcga  900
ctcatcaaca acaactgggg attccggcct aagcgactca acttcaagct cttcaacatt  960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caaagaagga gaggaccgtt tctttccttt gtctggatct  1620
ttaatttttg gcaaacaagg aactggaaga gacaacgtgg atgcggacaa agtcatgata  1680
accaacgaag aagaaattaa aactactaac ccggtagcaa cggagtccta tggacaagtg  1740
gccacaaacc accagagtgc ccaagcacag gcgcagaccg gctgggttca aaaccaagga  1800
atgcttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcacccgc ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa aacagcaagc gctggaaccc ggagatccag  2100
tacacttcca actattacaa gtctaataat gttgaatttg ctgttaatac tgaaggtgta  2160
tatagtgaac cccgccccat tggcaccaga tacctgactc gtaatctgta a           2211

SEQ ID NO: 9             moltype = AA  length = 599
FEATURE                  Location/Qualifiers
source                   1..599
                         mol_type = protein
                         organism = Adeno-associated dependoparvovirus A
SEQUENCE: 9
TAPGKKRPVE QSPQEPDSSA GIGKSGAQPA KKRLNFGQTG DTESVPDPQP IGEPPAAPSG  60
VGSLTMASGG GAPVADNNEG ADGVGSSSGN WHCDSQWLGD RVITTSTRTW ALPTYNNHLY  120
KQISNSTSGG SSNDNAYFGY STPWGYFDFN RFHCHFSPRD WQRLINNNWG FRPKRLNFKL  180
FNIQVKEVTD NNGVKTIANN LTSTVQVFTD SDYQLPYVLG SAHEGCLPPF PADVFMIPQY  240
GYLTLNDGSQ AVGRSSFYCL EYFPSQMLRT GNNFQFSYEF ENVPFHSSYA HSQSLDRLMN  300
PLIDQYLYYL SKTINGSGQN QQTLKFSVAG PSNMAVQGRN YIPGPSYRQQ RVSTTVTQNN  360
NSEFAWPGAS SWALNGRNSL MNPGPAMASH KEGEDRFFPL SGSLIFGKQG TGRDNVDADK  420
VMITNEEEIK TTNPVATESY GQVATNHQSA QAQAQTGWVQ NQGILPGMVW QDRDVYLQGP  480
IWAKIPHTDG NFHPSPLMGG FGMKHPPPQI LIKNTPVPAD PPTAFNKDKL NSFITQYSTG  540
QVSVEIEWEL QKENSKRWNP EIQYTSNYYK SNNVEFAVNT EGVYSEPRPI GTRYLTRNL   599

SEQ ID NO: 10            moltype = AA  length = 599
FEATURE                  Location/Qualifiers
source                   1..599
```

```
                        mol_type = protein
                        organism = synthetic construct
SEQUENCE: 10
TAPGKKRPVE QSPQEPDSSA GIGKSGAQPA KKRLNFGQTG DTESVPDPQP IGEPPAAPSG  60
VGSLTMASGG GAPVADNNEG ADGVGSSSGN WHCDSQWLGD RVITTSTRTW ALPTYNNHLY  120
KQISNSTSGG SSNDNAYFGY STPWGYFDFN RFHCHFSPRD WQRLINNNWG FRPKRLNFKL  180
FNIQVKEVTD NNGVKTIANN LTSTVQVFTD SDYQLPYVLG SAHEGCLPPF PADVFMIPQY  240
GYLTLNDGSQ AVGRSSFYCL EYFPSQMLRT GNNFQFSYEF ENVPWHSSYA HSQSLDRLMN  300
PLIDQYLYYL SKTINGSGQN QQTLKFSVAG PSNMAVQGRN YIPGPSYRQQ RVSTTVTQNN  360
NSEFAWPGAS SWALNGRNSL MNPGPAMASH KEGEDRFFPL SGSLIFGKQG TGRDNVDADK  420
VMITNEEEIK TTNPVATESY GQVATNHQSA QAQAQTGWVQ NQGILPGMVW QDRDVYLQGP  480
IWAKIPHTDG NFHPSPLMGG FGMKHPPPQI LIKNTPVPAD PPTAFNKDKL NSFITQYSTG  540
QVSVEIEWEL QKENSKRWNP EIQYTSNYYK SNNVEFAVNT EGVYSEPRPI GTRYLTRNL   599

SEQ ID NO: 11           moltype = AA  length = 599
FEATURE                 Location/Qualifiers
source                  1..599
                        mol_type = protein
                        organism = synthetic construct
SEQUENCE: 11
TAPGKKRPVE QSPQEPDSSA GIGKSGAQPA KKRLNFGQTG DTESVPDPQP IGEPPAAPSG  60
VGSLTMASGG GAPVADNNEG ADGVGSSSGN WHCDSQWLGD RVITTSTRTW ALPTYNNHLY  120
KQISNSTSGG SSNDNAYFGY STPWGYFDFN RFHCHFSPRD WQRLINNNWG FRPKRLNFKL  180
FNIQVKEVTD NNGVKTIANN LTSTVQVFTD SDYQLPYVLG SAHEGCLPPF PADVFMIPQY  240
GYLTLNDGSQ AVGRSSFYCL EYFPSQMLRT GNNFQFSYEF ENVPWHSSYA HSQSLDRLMN  300
PLIDQYLYFL SKTINGSGQN QQTLKFSVAG PSNMAVQGRN YIPGPSYRQQ RVSTTVTQNN  360
NSEFAWPGAS SWALNGRNSL MNPGPAMASH KEGEDRFFPL SGSLIFGKQG TGRDNVDADK  420
VMITNEEEIK TTNPVATESY GQVATNHQSA QAQAQTGWVQ NQGILPGMVW QDRDVYLQGP  480
IWAKIPHTDG NFHPSPLMGG FGMKHPPPQI LIKNTPVPAD PPTAFNKDKL NSFITQYSTG  540
QVSVEIEWEL QKENSKRWNP EIQYTSNYYK SNNVEFAVNT EGVYSEPRPI GTRYLTRNL   599

SEQ ID NO: 12           moltype = AA  length = 599
FEATURE                 Location/Qualifiers
source                  1..599
                        mol_type = protein
                        organism = synthetic construct
SEQUENCE: 12
TAPGKKRPVE QSPQEPDSSA GIGKSGAQPA KKRLNFGQTG DTESVPDPQP IGEPPAAPSG  60
VGSLTMASGG GAPVADNNEG ADGVGSSSGN WHCDSQWLGD RVITTSTRTW ALPTYNNHLY  120
KQISNSTSGG SSNDNAYFGY STPWGYFDFN RFHCHFSPRD WQRLINNNWG FRPKRLNFKL  180
FNIQVKEVTD NNGVKTIANN LTSTVQVFTD SDYQLPYVLG SAHEGCLPPF PADVFMIPQY  240
GYLTLNDGSQ AVGRSSFYCL EYFPSQMLRT GNNFQFSYEF ENVPFHSSYA HSQSLDRLMN  300
PLIDQYLYYL SKTINGSGQN QQTLKFSVAG PSNMAVQGRN YIPGPSYRQQ RVSTTVTQNN  360
NSEFAWPGAS SWALNGRNSL MNPGPAMASH KEGEDRFFPL SGSLIFGKQG TGRDNVDADK  420
VMITNEEEIK TTNPVATESY GQVATNHQSA QAQAQTGWVQ NQGMLPGMVW QDRDVYLQGP  480
IWAKIPHTDG NFHPSPLMGG FGMKHPPPQI LIKNTPVPAD PPTAFNKDKL NSFITQYSTG  540
QVSVEIEWEL QKENSKRWNP EIQYTSNYYK SNNVEFAVNT EGVYSEPRPI GTRYLTRNL   599

SEQ ID NO: 13           moltype = DNA  length = 1800
FEATURE                 Location/Qualifiers
source                  1..1800
                        mol_type = genomic DNA
                        organism = Adeno-associated dependoparvovirus A
SEQUENCE: 13
acggctcctg gaaagaagag gcctgtagag cagtctcctc aggaaccgga ctcctccgcg  60
ggtattggca aatcgggtgc acagcccgct aaaaagagac tcaatttcgg tcagactggc  120
gacacagagt cagtcccaga ccctcaacca atcggagaac ctcccgcagc cccctcaggt  180
gtgggatctc ttacaatggc ttcaggtggt ggcgcaccag tggcagacaa taacgaaggt  240
gccgatggag tgggtagttc ctcgggaaat tggcattgcg attcccaatg gctgggggac  300
agagtcatca ccaccagcac ccgaacctgg gccctgccca cctacaacaa tcacctctac  360
aagcaaatct ccaacagcac atctggagga tcttcaaatg acaacgccta cttcggctac  420
agcacccccct gggggtattt tgacttcaac agattccact gccacttctc accacgtgac  480
tggcagcgac tcatcaacaa caactgggga ttccggccta agcgactcaa cttcaagctc  540
ttcaacattc aggtcaaaga ggttacggac aacaatggag tcaagaccat cgccaataac  600
cttaccagca cggtccaggt cttcacggac tcagactatc agctcccgta cgtgctcggg  660
tcggctcacg agggctgcct cccgccgttc ccagcggacg ttttcatgat tcctcagtac  720
gggtatctga cgcttaatga tggaagccag gccgtgggtc gttcgtcctt ttactgcctg  780
gaatatttcc cgtcgcaaat gctaagaacg ggtaacaact tccagttcag ctacgagttt  840
gagaacgtac ctttccatag cagctacgct cacagccaaa gcctggaccg actaatgaat  900
ccactcatcg accaatactt gtactatctc tcaaagacta ttaacggttc tggacagaat  960
caacaaacgc taaaattcag tgtggccgga cccagcaaca tggctgtcca gggaagaaac  1020
tacatacctg gacccagcta ccgacaacaa cgtgtctcaa ccactgtgac tcaaaacaac  1080
aacagcgaat ttgcttggcc tggagcttct tcttgggctc tcaatggacg taatagcttg  1140
atgaatcctg gacctgctat ggccagccac aaagaaggag aggaccgttt ctttcctttg  1200
tctggatctt taatttttgg caaacaagga actggaagag acaacgtgga tgcggacaaa  1260
gtcatgataa ccaacgaaga agaaattaaa actactaacc cggtagcaac ggagtcctat  1320
ggacaagtgg ccacaaacca ccagagtgcc caagcacagg cgcagaccgg ctgggttcaa  1380
aaccaaggaa tacttccggg tatggtttgg caggacagag atgtgtacct gcaaggaccc  1440
atttgggcca aaattcctca cacggacggc aactttcacc cttctccgct gatgggaggg  1500
```

```
tttggaatga agcacccgcc tcctcagatc ctcatcaaaa acacacctgt acctgcggat  1560
cctccaacgg ccttcaacaa ggacaagctg aactctttca tcacccagta ttctactggc  1620
caagtcagcg tggagatcga gtgggagctg cagaaggaaa acagcaagcg ctggaacccg  1680
gagatccagt acacttccaa ctattacaag tctaataatg ttgaatttgc tgttaatact  1740
gaaggtgtat atagtgaacc ccgccccatt ggcaccagat acctgactcg taatctgtaa  1800

SEQ ID NO: 14          moltype = DNA  length = 1800
FEATURE                Location/Qualifiers
source                 1..1800
                       mol_type = other DNA
                       organism = synthetic construct
SEQUENCE: 14
acggctcctg gaaagaagag gcctgtagag cagtctcctc aggaaccgga ctcctccgcg  60
ggtattggca aatcgggtgc acagcccgct aaaaagagac tcaatttcgg tcagactggc  120
gacacagagt cagtcccaga ccctcaacca atcggagaac ctcccgcagc cccctcaggt  180
gtgggatctc ttacaatggc ttcaggtggt ggcgcaccag tggcagacaa taacgaaggt  240
gccgatggag tgggtagttc ctcgggaaat tggcattgcg attcccaatg gctgggggac  300
agagtcatca ccaccagcac ccgaacctgg gccctgccca cctacaacaa tcacctctac  360
aagcaaatct ccaacagcac atctggagga tcttcaaatg acaacgccta cttcggctac  420
agcacccccct gggggtattt tgacttcaac agattccact gccacttctc accacgtgac  480
tggcagcgac tcatcaacaa caactgggga ttccggccta agcgactcaa cttcaagctc  540
ttcaacattc aggtcaaaga ggttacggac aacaatggag tcaagaccat cgccaataac  600
cttaccagca cggtccaggt cttcacggac tcagactatc agctcccgta cgtgctcggg  660
tcggctcacg agggctgcct cccgccgttc ccagcggacg ttttcatgat tcctcagtac  720
gggtatctga cgcttaatga tggaagccag gccgtgggtc gttcgtcctt ttactgcctg  780
gaatatttcc cgtcgcaaat gctaagaacg ggtaacaact tccagttcag ctacgagttt  840
gagaacgtac cttggcatag cagctacgct cacagccaaa gcctggaccg actaatgaat  900
ccactcatcg accaatactt gtactatctc tcaaagacta ttaacggttc tggacagaat  960
caacaaacgc taaaattcag tgtggccgga cccagcaaca tggctgtcca gggaagaaac  1020
tacatacctg gacccagcta ccgacaacaa cgtgtctcaa ccactgtgac tcaaaacaac  1080
aacagcgaat ttgcttggcc tggagcttct tcttgggctc tcaatggacg taatagcttg  1140
atgaatcctg gacctgctat ggccagccac aaagaaggag aggaccgttt ctttcctttg  1200
tctggatctt taatttttgg caaacaagga actggaagag acaacgtgga tgcggacaaa  1260
gtcatgataa ccaacgaaga agaaattaaa actactaacc cggtagcaac ggagtcctat  1320
ggacaagtgg ccacaaacca ccagagtgcc caagcacagg cgcagaccgg ctgggttcaa  1380
aaccaaggaa tacttccggg tatggtttgg caggacagag atgtgtacct gcaaggaccc  1440
atttgggcca aaattcctca cacggacggc aactttcacc cttctccgct gatgggaggg  1500
tttggaatga agcacccgcc tcctcagatc ctcatcaaaa acacacctgt acctgcggat  1560
cctccaacgg ccttcaacaa ggacaagctg aactctttca tcacccagta ttctactggc  1620
caagtcagcg tggagatcga gtgggagctg cagaaggaaa acagcaagcg ctggaacccg  1680
gagatccagt acacttccaa ctattacaag tctaataatg ttgaatttgc tgttaatact  1740
gaaggtgtat atagtgaacc ccgccccatt ggcaccagat acctgactcg taatctgtaa  1800

SEQ ID NO: 15          moltype = DNA  length = 1800
FEATURE                Location/Qualifiers
source                 1..1800
                       mol_type = other DNA
                       organism = synthetic construct
SEQUENCE: 15
acggctcctg gaaagaagag gcctgtagag cagtctcctc aggaaccgga ctcctccgcg  60
ggtattggca aatcgggtgc acagcccgct aaaaagagac tcaatttcgg tcagactggc  120
gacacagagt cagtcccaga ccctcaacca atcggagaac ctcccgcagc cccctcaggt  180
gtgggatctc ttacaatggc ttcaggtggt ggcgcaccag tggcagacaa taacgaaggt  240
gccgatggag tgggtagttc ctcgggaaat tggcattgcg attcccaatg gctgggggac  300
agagtcatca ccaccagcac ccgaacctgg gccctgccca cctacaacaa tcacctctac  360
aagcaaatct ccaacagcac atctggagga tcttcaaatg acaacgccta cttcggctac  420
agcacccccct gggggtattt tgacttcaac agattccact gccacttctc accacgtgac  480
tggcagcgac tcatcaacaa caactgggga ttccggccta agcgactcaa cttcaagctc  540
ttcaacattc aggtcaaaga ggttacggac aacaatggag tcaagaccat cgccaataac  600
cttaccagca cggtccaggt cttcacggac tcagactatc agctcccgta cgtgctcggg  660
tcggctcacg agggctgcct cccgccgttc ccagcggacg ttttcatgat tcctcagtac  720
gggtatctga cgcttaatga tggaagccag gccgtgggtc gttcgtcctt ttactgcctg  780
gaatatttcc cgtcgcaaat gctaagaacg ggtaacaact tccagttcag ctacgagttt  840
gagaacgtac cttggcatag cagctacgct cacagccaaa gcctggaccg actaatgaat  900
ccactcatcg accaatactt gtactttctc tcaaagacta ttaacggttc tggacagaat  960
caacaaacgc taaaattcag tgtggccgga cccagcaaca tggctgtcca gggaagaaac  1020
tacatacctg gacccagcta ccgacaacaa cgtgtctcaa ccactgtgac tcaaaacaac  1080
aacagcgaat ttgcttggcc tggagcttct tcttgggctc tcaatggacg taatagcttg  1140
atgaatcctg gacctgctat ggccagccac aaagaaggag aggaccgttt ctttcctttg  1200
tctggatctt taatttttgg caaacaagga actggaagag acaacgtgga tgcggacaaa  1260
gtcatgataa ccaacgaaga agaaattaaa actactaacc cggtagcaac ggagtcctat  1320
ggacaagtgg ccacaaacca ccagagtgcc caagcacagg cgcagaccgg ctgggttcaa  1380
aaccaaggaa tacttccggg tatggtttgg caggacagag atgtgtacct gcaaggaccc  1440
atttgggcca aaattcctca cacggacggc aactttcacc cttctccgct gatgggaggg  1500
tttggaatga agcacccgcc tcctcagatc ctcatcaaaa acacacctgt acctgcggat  1560
cctccaacgg ccttcaacaa ggacaagctg aactctttca tcacccagta ttctactggc  1620
caagtcagcg tggagatcga gtgggagctg cagaaggaaa acagcaagcg ctggaacccg  1680
gagatccagt acacttccaa ctattacaag tctaataatg ttgaatttgc tgttaatact  1740
gaaggtgtat atagtgaacc ccgccccatt ggcaccagat acctgactcg taatctgtaa  1800
```

```
SEQ ID NO: 16           moltype = DNA  length = 1800
FEATURE                 Location/Qualifiers
source                  1..1800
                        mol_type = other DNA
                        organism = synthetic construct
SEQUENCE: 16
acggctcctg gaaagaagag gcctgtagag cagtctcctc aggaaccgga ctcctccgcg  60
ggtattggca aatcgggtgc acagcccgct aaaaagagac tcaatttcgg tcagactggc  120
gacacagagt cagtcccaga ccctcaacca atcggagaac ctcccgcagc cccctcaggt  180
gtgggatctc ttacaatggc ttcaggtggt ggcgcaccag tggcagacaa taacgaaggt  240
gccgatggag tgggtagttc ctcgggaaat tggcattgcg attcccaatg gctgggggac  300
agagtcatca ccaccagcac ccgaacctgg gccctgccca cctacaacaa tcacctctac  360
aagcaaatct ccaacagcac atctggagga tcttcaaatg acaacgccta cttcggctac  420
agcaccccct gggggtattt tgacttcaac agattccact gccacttctc accacgtgac  480
tggcagcgac tcatcaacaa caactgggga ttccggccta agcgactcaa cttcaagctc  540
ttcaacattc aggtcaaaga ggttacggac aacaatggag tcaagaccat cgccaataac  600
cttaccagca cggtccaggt cttcacggac tcagactatc agctcccgta cgtgctcggg  660
tcggctcacg agggctgcct cccgccgttc ccagcggacg ttttcatgat tcctcagtac  720
gggtatctga cgcttaatga tggaagccag gccgtgggtc gttcgtcctt ttactgcctg  780
gaatatttcc cgtcgcaaat gctaagaacg ggtaacaact tccagttcag ctacgagttt  840
gagaacgtac ctttccatag cagctacgct cacagccaaa gcctggaccg actaatgaat  900
ccactcatcg accaatactt gtactatctc tcaaagacta ttaacggttc tggacagaat  960
caacaaacgc taaaattcag tgtggccgga cccagcaaca tggctgtcca gggaagaaac  1020
tacatacctg gacccagcta ccgacaacaa cgtgtctcaa ccactgtgac tcaaaacaac  1080
aacagcgaat ttgcttggcc tggagcttct tcttgggctc tcaatggacg taatagcttg  1140
atgaatcctg gacctgctat ggccagccac aaagaaggag aggaccgttt ctttcctttg  1200
tctggatctt taatttttgg caaacaagga actggaagag acaacgtgga tgcggacaaa  1260
gtcatgataa ccaacgaaga agaaattaaa actactaacc cggtagcaac ggagtcctat  1320
ggacaagtgg ccacaaacca ccagagtgcc caagcacagg cgcagaccgg ctgggttcaa  1380
aaccaaggaa tgcttccggg tatggtttgg caggacagag atgtgtacct gcaaggaccc  1440
atttgggcca aaattcctca cacggacggc aactttcacc cttctccgct gatgggaggg  1500
tttggaatga agcacccgcc tcctcagatc ctcatcaaaa acacacctgt acctgcggat  1560
cctccaacgg ccttcaacaa ggacaagctg aactctttca tcacccagta ttctactggc  1620
caagtcagcg tggagatcga gtgggagctg cagaaggaaa acagcaagcg ctggaacccg  1680
gagatccagt acacttccaa ctattacaag tctaataatg ttgaatttgc tgttaatact  1740
gaaggtgtat atagtgaacc ccgccccatt ggcaccagat acctgactcg taatctgtaa  1800

SEQ ID NO: 17           moltype = AA  length = 534
FEATURE                 Location/Qualifiers
source                  1..534
                        mol_type = protein
                        organism = Adeno-associated dependoparvovirus A
SEQUENCE: 17
MASGGGAPVA DNNEGADGVG SSSGNWHCDS QWLGDRVITT STRTWALPTY NNHLYKQISN  60
STSGGSSNDN AYFGYSTPWG YFDFNRFHCH FSPRDWQRLI NNNWGFRPKR LNFKLFNIQV  120
KEVTDNNGVK TIANNLTSTV QVFTDSDYQL PYVLGSAHEG CLPPFPADVF MIPQYGYLTL  180
NDGSQAVGRS SFYCLEYFPS QMLRTGNNFQ FSYEFENVPF HSSYAHSQSL DRLMNPLIDQ  240
YLYYLSKTIN GSGQNQQTLK FSVAGPSNMA VQGRNYIPGP SYRQQRVSTT VTQNNNSEFA  300
WPGASSWALN GRNSLMNPGP AMASHKEGED RFFPLSGSLI FGKQGTGRDN VDADKVMITN  360
EEEIKTTNPV ATESYGQVAT NHQSAQAQAQ TGWVQNQGIL PGMVWQDRDV YLQGPIWAKI  420
PHTDGNFHPS PLMGGFGMKH PPPQILIKNT PVPADPPTAF NKDKLNSFIT QYSTGQVSVE  480
IEWELQKENS KRWNPEIQYT SNYYKSNNVE FAVNTEGVYS EPRPIGTRYL TRNL        534

SEQ ID NO: 18           moltype = AA  length = 534
FEATURE                 Location/Qualifiers
source                  1..534
                        mol_type = protein
                        organism = synthetic construct
SEQUENCE: 18
MASGGGAPVA DNNEGADGVG SSSGNWHCDS QWLGDRVITT STRTWALPTY NNHLYKQISN  60
STSGGSSNDN AYFGYSTPWG YFDFNRFHCH FSPRDWQRLI NNNWGFRPKR LNFKLFNIQV  120
KEVTDNNGVK TIANNLTSTV QVFTDSDYQL PYVLGSAHEG CLPPFPADVF MIPQYGYLTL  180
NDGSQAVGRS SFYCLEYFPS QMLRTGNNFQ FSYEFENVPW HSSYAHSQSL DRLMNPLIDQ  240
YLYYLSKTIN GSGQNQQTLK FSVAGPSNMA VQGRNYIPGP SYRQQRVSTT VTQNNNSEFA  300
WPGASSWALN GRNSLMNPGP AMASHKEGED RFFPLSGSLI FGKQGTGRDN VDADKVMITN  360
EEEIKTTNPV ATESYGQVAT NHQSAQAQAQ TGWVQNQGIL PGMVWQDRDV YLQGPIWAKI  420
PHTDGNFHPS PLMGGFGMKH PPPQILIKNT PVPADPPTAF NKDKLNSFIT QYSTGQVSVE  480
IEWELQKENS KRWNPEIQYT SNYYKSNNVE FAVNTEGVYS EPRPIGTRYL TRNL        534

SEQ ID NO: 19           moltype = AA  length = 534
FEATURE                 Location/Qualifiers
source                  1..534
                        mol_type = protein
                        organism = synthetic construct
SEQUENCE: 19
MASGGGAPVA DNNEGADGVG SSSGNWHCDS QWLGDRVITT STRTWALPTY NNHLYKQISN  60
STSGGSSNDN AYFGYSTPWG YFDFNRFHCH FSPRDWQRLI NNNWGFRPKR LNFKLFNIQV  120
KEVTDNNGVK TIANNLTSTV QVFTDSDYQL PYVLGSAHEG CLPPFPADVF MIPQYGYLTL  180
```

-continued

```
NDGSQAVGRS SFYCLEYFPS QMLRTGNNFQ FSYEFENVPW HSSYAHSQSL DRLMNPLIDQ  240
YLYFLSKTIN GSGQNQQTLK FSVAGPSNMA VQGRNYIPGP SYRQQRVSTT VTQNNNSEFA  300
WPGASSWALN GRNSLMNPGP AMASHKEGED RFFPLSGSLI FGKQGTGRDN VDADKVMITN  360
EEEIKTTNPV ATESYGQVAT NHQSAQAQAQ TGWVQNQGIL PGMVWQDRDV YLQGPIWAKI  420
PHTDGNFHPS PLMGGFGMKH PPPQILIKNT PVPADPPTAF NKDKLNSFIT QYSTGQVSVE  480
IEWELQKENS KRWNPEIQYT SNYYKSNNVE FAVNTEGVYS EPRPIGTRYL TRNL        534

SEQ ID NO: 20          moltype = AA  length = 534
FEATURE                Location/Qualifiers
source                 1..534
                       mol_type = protein
                       organism = synthetic construct
SEQUENCE: 20
MASGGGAPVA DNNEGADGVG SSSGNWHCDS QWLGDRVITT STRTWALPTY NNHLYKQISN  60
STSGGSSNDN AYFGYSTPWG YFDFNRFHCH FSPRDWQRLI NNNWGFRPKR LNFKLFNIQV  120
KEVTDNNGVK TIANNLTSTV QVFTDSDYQL PYVLGSAHEG CLPPFPADVF MIPQYGYLTL  180
NDGSQAVGRS SFYCLEYFPS QMLRTGNNFQ FSYEFENVPF HSSYAHSQSL DRLMNPLIDQ  240
YLYYLSKTIN GSGQNQQTLK FSVAGPSNMA VQGRNYIPGP SYRQQRVSTT VTQNNNSEFA  300
WPGASSWALN GRNSLMNPGP AMASHKEGED RFFPLSGSLI FGKQGTGRDN VDADKVMITN  360
EEEIKTTNPV ATESYGQVAT NHQSAQAQAQ TGWVQNQGML PGMVWQDRDV YLQGPIWAKI  420
PHTDGNFHPS PLMGGFGMKH PPPQILIKNT PVPADPPTAF NKDKLNSFIT QYSTGQVSVE  480
IEWELQKENS KRWNPEIQYT SNYYKSNNVE FAVNTEGVYS EPRPIGTRYL TRNL        534

SEQ ID NO: 21          moltype = DNA  length = 1605
FEATURE                Location/Qualifiers
source                 1..1605
                       mol_type = genomic DNA
                       organism = Adeno-associated dependoparvovirus A
SEQUENCE: 21
atggcttcag gtggtggcgc accagtggca gacaataacg aaggtgccga tggagtgggt  60
agttcctcgg gaaattggca ttgcgattcc caatggctgg gggacagagt catcaccacc  120
agcacccgaa cctgggccct gcccacctac aacaatcacc tctacaagca aatctccaac  180
agcacatctg gaggatcttc aaatgacaac gcctacttcg gctacagcac cccctggggg  240
tattttgact tcaacagatt ccactgccac ttctcaccac gtgactggca gcgactcatc  300
aacaacaact ggggattccg gcctaagcga ctcaacttca agctcttcaa cattcaggtc  360
aaagaggtta cggacaacaa tggagtcaag accatcgcca ataaccttac cagcacggtc  420
caggtcttca cggactcaga ctatcagctc ccgtacgtgc tcgggtcggc tcacgagggc  480
tgcctcccgc cgttcccagc ggacgttttc atgattcctc agtacgggta tctgacgctt  540
aatgatggaa gccaggccgt gggtcgttcg tccttttact gcctggaata tttcccgtcg  600
caaatgctaa gaacgggtaa caacttccag ttcagctacg agtttgagaa cgtacctttc  660
catagcagct acgctcacag ccaaagcctg gaccgactaa tgaatccact catcgaccaa  720
tacttgtact atctctcaaa gactattaac ggttctggac agaatcaaca aacgctaaaa  780
ttcagtgtgg ccggacccag caacatggct gtccagggaa gaaactacat acctggaccc  840
agctaccgac aacaacgtgt ctcaaccact gtgactcaaa acaacaacag cgaatttgct  900
tggcctggag cttcttcttg ggctctcaat ggacgtaata gcttgatgaa tcctggacct  960
gctatggcca gccacaaaga aggagaggac cgtttctttc ctttgtctgg atctttaatt  1020
tttggcaaac aaggaactgg aagagacaac gtggatgcgg acaaagtcat gataaccaac  1080
gaagaagaaa ttaaaactac taacccggta gcaacggagt cctatggaca agtggccaca  1140
aaccaccaga gtgcccaagc acaggcgcag accggctggg ttcaaaacca aggaatactt  1200
ccgggtatgg tttggcagga cagagatgtg tacctgcaag gacccatttg ggccaaaatt  1260
cctcacacgg acggcaactt tcacccttct ccgctgatgg gagggtttgg aatgaagcac  1320
ccgcctcctc agatcctcat caaaaacaca cctgtacctg cggatcctcc aacggccttc  1380
aacaaggaca agctgaactc tttcatcacc cagtattcta ctggccaagt cagcgtggag  1440
atcgagtggg agctgcagaa ggaaaacagc aagcgctgga acccggagat ccagtacact  1500
tccaactatt acaagtctaa taatgttgaa tttgctgtta atactgaagg tgtatatagt  1560
gaaccccgcc ccattggcac cagatacctg actcgtaatc tgtaa                  1605

SEQ ID NO: 22          moltype = DNA  length = 1605
FEATURE                Location/Qualifiers
source                 1..1605
                       mol_type = other DNA
                       organism = synthetic construct
SEQUENCE: 22
atggcttcag gtggtggcgc accagtggca gacaataacg aaggtgccga tggagtgggt  60
agttcctcgg gaaattggca ttgcgattcc caatggctgg gggacagagt catcaccacc  120
agcacccgaa cctgggccct gcccacctac aacaatcacc tctacaagca aatctccaac  180
agcacatctg gaggatcttc aaatgacaac gcctacttcg gctacagcac cccctggggg  240
tattttgact tcaacagatt ccactgccac ttctcaccac gtgactggca gcgactcatc  300
aacaacaact ggggattccg gcctaagcga ctcaacttca agctcttcaa cattcaggtc  360
aaagaggtta cggacaacaa tggagtcaag accatcgcca ataaccttac cagcacggtc  420
caggtcttca cggactcaga ctatcagctc ccgtacgtgc tcgggtcggc tcacgagggc  480
tgcctcccgc cgttcccagc ggacgttttc atgattcctc agtacgggta tctgacgctt  540
aatgatggaa gccaggccgt gggtcgttcg tccttttact gcctggaata tttcccgtcg  600
caaatgctaa gaacgggtaa caacttccag ttcagctacg agtttgagaa cgtaccttgg  660
catagcagct acgctcacag ccaaagcctg gaccgactaa tgaatccact catcgaccaa  720
tacttgtact atctctcaaa gactattaac ggttctggac agaatcaaca aacgctaaaa  780
ttcagtgtgg ccggacccag caacatggct gtccagggaa gaaactacat acctggaccc  840
agctaccgac aacaacgtgt ctcaaccact gtgactcaaa acaacaacag cgaatttgct  900
tggcctggag cttcttcttg ggctctcaat ggacgtaata gcttgatgaa tcctggacct  960
```

-continued

```
gctatggcca gccacaaaga aggagaggac cgtttctttc ctttgtctgg atctttaatt  1020
tttggcaaac aaggaactgg aagagacaac gtggatgcgg acaaagtcat gataaccaac  1080
gaagaagaaa ttaaaactac taacccggta gcaacggagt cctatggaca agtggccaca  1140
aaccaccaga gtgcccaagc acaggcgcag accggctggg ttcaaaacca aggaatactt  1200
ccgggtatgg tttggcagga cagagatgtg tacctgcaag gacccatttg ggccaaaatt  1260
cctcacacgg acggcaactt tcacccttct ccgctgatgg gagggtttgg aatgaagcac  1320
ccgcctcctc agatcctcat caaaaacaca cctgtacctg cggatcctcc aacggccttc  1380
aacaaggaca agctgaactc tttcatcacc cagtattcta ctggccaagt cagcgtggag  1440
atcgagtggg agctgcagaa ggaaaacagc aagcgctgga acccggagat ccagtacact  1500
tccaactatt acaagtctaa taatgttgaa tttgctgtta atactgaagg tgtatatagt  1560
gaaccccgcc ccattggcac cagatacctg actcgtaatc tgtaa                    1605

SEQ ID NO: 23           moltype = DNA  length = 1605
FEATURE                 Location/Qualifiers
source                  1..1605
                        mol_type = other DNA
                        organism = synthetic construct
SEQUENCE: 23
atggcttcag gtggtggcgc accagtggca gacaataacg aaggtgccga tggagtgggt  60
agttcctcgg gaaattggca ttgcgattcc caatggctgg gggacagagt catcaccacc  120
agcacccgaa cctgggccct gcccacctac aacaatcacc tctacaagca aatctccaac  180
agcacatctg gaggatcttc aaatgacaac gcctacttcg gctacagcac cccctggggg  240
tattttgact tcaacagatt ccactgccac ttctcaccac gtgactggca gcgactcatc  300
aacaacaact ggggattccg gcctaagcga ctcaacttca agctcttcaa cattcaggtc  360
aaagaggtta cggacaacaa tggagtcaag accatcgcca ataaccttac cagcacggtc  420
caggtcttca cggactcaga ctatcagctc ccgtacgtgc tcgggtcggc tcacgagggc  480
tgcctcccgc cgttcccagc ggacgttttc atgattcctc agtacgggta tctgacgctt  540
aatgatggaa gccaggccgt gggtcgttcg tccttttact gcctggaata tttcccgtcg  600
caaatgctaa gaacgggtaa caacttccag ttcagctacg agtttgagaa cgtaccttgg  660
catagcagct acgctcacag ccaaagcctg gaccgactaa tgaatccact catcgaccaa  720
tacttgtact ttctctcaaa gactattaac ggttctggac agaatcaaca aacgctaaaa  780
ttcagtgtgg ccggacccag caacatggct gtccagggaa gaaactacat acctggaccc  840
agctaccgac aacaacgtgt ctcaaccact gtgactcaaa acaacaacag cgaatttgct  900
tggcctggag cttcttcttg ggctctcaat ggacgtaata gcttgatgaa tcctggacct  960
gctatggcca gccacaaaga aggagaggac cgtttctttc ctttgtctgg atctttaatt  1020
tttggcaaac aaggaactgg aagagacaac gtggatgcgg acaaagtcat gataaccaac  1080
gaagaagaaa ttaaaactac taacccggta gcaacggagt cctatggaca agtggccaca  1140
aaccaccaga gtgcccaagc acaggcgcag accggctggg ttcaaaacca aggaatactt  1200
ccgggtatgg tttggcagga cagagatgtg tacctgcaag gacccatttg ggccaaaatt  1260
cctcacacgg acggcaactt tcacccttct ccgctgatgg gagggtttgg aatgaagcac  1320
ccgcctcctc agatcctcat caaaaacaca cctgtacctg cggatcctcc aacggccttc  1380
aacaaggaca agctgaactc tttcatcacc cagtattcta ctggccaagt cagcgtggag  1440
atcgagtggg agctgcagaa ggaaaacagc aagcgctgga acccggagat ccagtacact  1500
tccaactatt acaagtctaa taatgttgaa tttgctgtta atactgaagg tgtatatagt  1560
gaaccccgcc ccattggcac cagatacctg actcgtaatc tgtaa                    1605

SEQ ID NO: 24           moltype = DNA  length = 1605
FEATURE                 Location/Qualifiers
source                  1..1605
                        mol_type = other DNA
                        organism = synthetic construct
SEQUENCE: 24
atggcttcag gtggtggcgc accagtggca gacaataacg aaggtgccga tggagtgggt  60
agttcctcgg gaaattggca ttgcgattcc caatggctgg gggacagagt catcaccacc  120
agcacccgaa cctgggccct gcccacctac aacaatcacc tctacaagca aatctccaac  180
agcacatctg gaggatcttc aaatgacaac gcctacttcg gctacagcac cccctggggg  240
tattttgact tcaacagatt ccactgccac ttctcaccac gtgactggca gcgactcatc  300
aacaacaact ggggattccg gcctaagcga ctcaacttca agctcttcaa cattcaggtc  360
aaagaggtta cggacaacaa tggagtcaag accatcgcca ataaccttac cagcacggtc  420
caggtcttca cggactcaga ctatcagctc ccgtacgtgc tcgggtcggc tcacgagggc  480
tgcctcccgc cgttcccagc ggacgttttc atgattcctc agtacgggta tctgacgctt  540
aatgatggaa gccaggccgt gggtcgttcg tccttttact gcctggaata tttcccgtcg  600
caaatgctaa gaacgggtaa caacttccag ttcagctacg agtttgagaa cgtacctttc  660
catagcagct acgctcacag ccaaagcctg gaccgactaa tgaatccact catcgaccaa  720
tacttgtact atctctcaaa gactattaac ggttctggac agaatcaaca aacgctaaaa  780
ttcagtgtgg ccggacccag caacatggct gtccagggaa gaaactacat acctggaccc  840
agctaccgac aacaacgtgt ctcaaccact gtgactcaaa acaacaacag cgaatttgct  900
tggcctggag cttcttcttg ggctctcaat ggacgtaata gcttgatgaa tcctggacct  960
gctatggcca gccacaaaga aggagaggac cgtttctttc ctttgtctgg atctttaatt  1020
tttggcaaac aaggaactgg aagagacaac gtggatgcgg acaaagtcat gataaccaac  1080
gaagaagaaa ttaaaactac taacccggta gcaacggagt cctatggaca agtggccaca  1140
aaccaccaga gtgcccaagc acaggcgcag accggctggg ttcaaaacca aggaatgctt  1200
ccgggtatgg tttggcagga cagagatgtg tacctgcaag gacccatttg ggccaaaatt  1260
cctcacacgg acggcaactt tcacccttct ccgctgatgg gagggtttgg aatgaagcac  1320
ccgcctcctc agatcctcat caaaaacaca cctgtacctg cggatcctcc aacggccttc  1380
```

-continued

```
aacaaggaca agctgaactc tttcatcacc cagtattcta ctggccaagt cagcgtggag  1440
atcgagtggg agctgcagaa ggaaaacagc aagcgctgga acccggagat ccagtacact  1500
tccaactatt acaagtctaa taatgttgaa tttgctgtta atactgaagg tgtatatagt  1560
gaaccccgcc ccattggcac cagatacctg actcgtaatc tgtaa                  1605
```